US005726025A

United States Patent [19]
Kirschner et al.

[11] Patent Number: 5,726,025
[45] Date of Patent: Mar. 10, 1998

[54] ASSAY AND REAGENTS FOR DETECTING INHIBITORS OF UBIQUITIN-DEPENDENT DEGRADATION OF CELL CYCLE REGULATORY PROTEINS

[75] Inventors: Marc W. Kirschner, Newton; Randall W. King; Jan-Michael Peters, both of Brookline, all of Mass.

[73] Assignee: President and Fellows of Harvard College, Cambridge, Mass.

[21] Appl. No.: 425,299

[22] Filed: Apr. 20, 1995

[51] Int. Cl.$^6$ ............................ C12Q 1/48; G01N 33/567
[52] U.S. Cl. ........................ 435/7.2; 435/7.23; 435/7.7; 435/7.9; 435/15; 435/172.3; 436/86; 436/503
[58] Field of Search .............................. 435/7.2, 7.23, 435/7.7, 7.9, 15, 172.3; 436/86, 503

[56] References Cited

U.S. PATENT DOCUMENTS 5,384,255  1/1995  Ciechanover et al. ................... 435/193

FOREIGN PATENT DOCUMENTS

92/20804  11/1992  WIPO.
95/18974  7/1995  WIPO.

OTHER PUBLICATIONS

Amon, A., et al., "Closing the Cell Cycle in Yeast: G2 Cyclin Proteolysis Initiated at Mitosis Persists until the Activation of G1 Cyclins in the Next Cycle", *Cell* 77:1037–1050 (1994).
Bailly, E., et al., "Cytoplasmic accumulation of cyclin B1 in human cells: association with a detergent–resistant compartment and with the centrosome", *J. Cell Sci.* 101:529–545 (1992).
Band, V., et al., "Loss of p53 Protein in Human Papillomavirus Type 16 E6–Immortalized Human Mammary Epithelial Cells", *J. Virol.* 65:6671–6676 (1991).
Berleth, E.S., et al., "Inhibition of Ubiquitin–Protein Ligase (E3) by Mono– and Bifunctional Phenylarsenoxides", *J. Biol. Chem.* 267:16403–16411 (1992).
Bissonnette, R.P., et al., "Apoptotic cell death induced by c–myc is inhibited by bcl–2", *Nature* 359:552–556 (1992).
Chen, P., et al., "Multiple Ubiquitin–Conjugating Enzymes Participate in the In Vivo Degradation of the Yeast Matα2 Repressor", *Cell* 74:357–369 (1993).
Ciechanover, A., "The Ubiquitin–Proteasome Proteolytic Pathway", *Cell* 79:13–21 (1994).
Cook, W.J., et al., "Structure of a Diubiquitin Conjugate and a Model for Interaction with Ubiquitin Conjgating Enzyme (E2)", *J. Biol. Chem.*, 267:16467–16471 (1992).
Cook, W.J., et al., "Tertiary Structure of Class I Ubiquitin–Conjugating Enzymes Are highly Conserved: Crystal Structure of Yeast Ubc4", *Biochem.* 32:13809–13817 (1993).
Crook, T., et al., "Degradation of p53 Can Be Targeted by HPV E6 Sequences Distinct from Those Required for p53 Binding and Trans–Activation", *Cell* 67:547–556 (1991).

Debec, A., et al., "Cyclin B is associated with centrosomes in *Drosophilia* mitotic cells", *Biol. Cell.* 101:121–126 (1992).
Dohmen, R.J., et al., "The N–end rule is mediated by the UBC2(RAD6) ubiquitin–conjugating enzyme", *Proc. Natl. Acad. Sci. USA* 88:7351–7355 (1991).
Ellison, M.J. et al., "Epitope–tagged Ubiquitin", *J. Biol. Chem.* 266:21150–21157 (1991).
Engle, D.B., et al., "Cell–Cycle Modulation of MPM–2–Specific Spindle Pole Body Phosphorylation in *Aspergillus nidulans*", *Cell Motility and the Cytoskeleton* 10:432–437 (1988).
Evan, G.I., et al., "Induction of Apoptosis in Fibroblasts by c–myc Protein", *Cell* 69:119–128 (1992).
Eytan, E., et al., "Ubiquitin C–terminal Hydrolase Activity Associated with the 26 S Protease Complex", *J. Biol. Chem.* 268:4668–4674 (1993).
Fankhauser, C., et al., "The *S. pombe cdc16* gene is required both for maintenance of p34$^{cdc2}$ kinase activity and regulation of septum formation: a link between mitosis and cytokinesis?", *EMBO J.* 12:2697–2704 (1993).
Félix, M–A., et al., "Triggering of cyclin degradation in interphase extracts of amphibian eggs by cdc2 kinase", *Nature* 346:379–382 (1990).
Girod, P–A., et al., "A Major Ubiquitin Conjugaton System in Wheat Germ Extracts Involves a 15–kDA Ubiquitin–conjugating Enzyme (E2) Homologous to the Yeast UBC4/UBC5 Gene Products", *J. Biol. Chem.* 268:955–960 (1993).
Glotzer, M., et al., "Cyclin is degraded by the ubiquitin pathway", *Nature* 349:132–138 (1991).
Hatfield, P.M., "Cloning of Ubiquitin Activating Enzyme from Wheat and Expression of a Functional Protein in *Escherichia coli*", *J. Biol. Chem.* 265:15813–15817 (1990).

(List continued on next page.)

Primary Examiner—David Saunders
Attorney, Agent, or Firm—Matthew P. Vincent; Beth E. Arnold; Foley, Hoag & Eliot LLP

[57] ABSTRACT

The present invention provides a systematic and practical approach for the identification of candidate agents able to inhibit ubiquitin-mediated degradation of a cell-cycle regulatory protein, such as cyclins. One aspect of the present invention relates to a method for identifying an inhibitor of ubiquitin-mediated proteolysis of a cell-cycle regulatory protein by (i) providing a ubiquitin-conjugating system that includes the regulatory protein and ubiquitin under conditions which promote the ubiquitination of the target protein, and (ii) measuring the level of ubiquitination of the subject protein brought about by the system in the presence and absence of a candidate agent. A decrease in the level of ubiquitin conjugation is indicative of an inhibitory activity for the candidate agent. The level of ubiquitination of the regulatory protein can be measured by determining the actual concentration of protein:ubiquitin conjugates formed; or inferred by detecting some other quality of the subject protein affected by ubiquitination, including the proteolytic degradation of the protein.

30 Claims, 2 Drawing Sheets

OTHER PUBLICATIONS

Hershko, A., et al., "Components of Ubiquitin–Protein Ligase System", *J. Biol. Chem.* 258:8206–8214 (1983).

Hershko, A., et al., "Components of a System That Ligates Cyclin to Ubiquitin and Their Regulation by the Protein Kinase cdc2", *J. Biol. Chem.* 269:4940–4946 (1994).

Hochstrasser, M., et al., "In Vivo Degradation of a Transcriptional Regulator: The Yeast α2 Repressor", *Cell* 61:697–708 (1990).

Hoefer, M., et al., "Purification and partial characterization of ubiquitin–activating enyme from *Saccharomyces cerevisiae*", *FEBS* 289:54–58 (1991)

Holloway, S.L., et al., "Anaphase Is Initiated by Proteolysis Rather Than by the Inactivation of Maturation–Promoting Factor", *Cell* 73:1393–1402 (1993).

Hughes, D.A., et al., "Molecular cloning and sequence analysis of cdc27+ required for the G2–M transition in the fission yeast *Schizosaccharomyces pombe*", *Mol. Gen. Genet.* 231:401–410 (1992).

Huibregtse, J.M., et al., "A cellular protein mediates association of p53 with the E6 oncoprotein of human papillomavirus types 16 or 18", *EMBO J.* 10:4129–4135 (1991).

Huibregtse, J.M., et al., "Cloning and Expression of the cDNA for E6–AP, a Protein That Mediates the Interaction of the Human Papillomavirus E6 Oncoprotein with p53", *Mol. Cell. Biol.* 13:775–784 (1993).

Hupp, T.R., et al., "Regulation of the Specific DNA Binding Function of p53", *Cell* 71:875–886 (1992).

Jacobs, Jr., W.R., et al., "Rapid Assessment of Drug Susceptibilities of *Mycobacterium tuberculosis* by Means of Luciferase Reporter Phages", *Science* 260:819–822 (1993).

Jentsch, S., "Ubiquitin–dependent protein degradation: a cellular perspective", *Trends in Cell Biol.* 2:98–103 (1992).

Jentsch, S., "The Ubiquitin–Conjugation System", *Annu. Rev. Genet.* 26:179–207 (1992).

Ketner, G., et al., "Efficient manipulation of the human adenovirus genome as an infectious yeast artifical chromosome clone", *Proc. Natl. Acad. Sci. USA* 91:6186–6190 (1994).

King, R.W., et al., "Mitosis in Transition", *Cell* 79:563–571 (1994).

Klemperer, N.S., et al., "A Novel, Arsenite–Sensitive E2 of the Ubiquitin Pathway: Purification and Properties", *Biochem.* 28:6035–6041 (1989).

Koken, M.H.M., et al., "Structural and functional conservation of two human homologs of the yeast DNA repair gene RAD6", *Proc. Natl. Acad. Sci. USA* 88:8865–8869 (1991).

Kuang, J., et al., "Multiple forms of maturation–promoting factor in unfertilized *Xenopus* eggs", *Proc. Natl. Acad. Sci. USA* 88:11530–11534 (1991).

Kuang, J. et al., "At Least Two Kinases Phosphorylate the MPM–2 Epitope during *Xenopus* Oocyte Maturation", *J. Cell Biol.* 123:859–868 (1993).

Kumagai, A., et al., "Regulation of the cdc25 Protein during the Cell Cycle in Xenopus Extracts", *Cell* 70:139–151 (1992).

Lamb, J.R., "Cdc16p, Cdc23p and Cdc27p form a complex essential for mitosis", *EMBO J.* 13:4321–4328 (1994).

Lorca, T., et al., "An Okadaic Acid–Sensitive Phosphatase Negatively Controls the Cyclin Degradation Pathway in Amphibian Eggs", *Mol. Cell. Biol.* 11:1171–1175 (1991).

Luca, F.C., et al., "Both Cyclin AΔ60 and BΔ97 are stable and arrest cells in M–phase, but only cyclin BΔ97 turns on cyclin destruction", *EMBO J.* 10:4311–4320 (1991).

Maldonado–Codina, G., et al., "Cyclins A and B Associate with Chromatin and the Polar Regions of Spindles, Respectively, and Do Not Undergo Complete Degradation at Anaphase in Syncytial *Drosphilia* Embryos", *J. Cell Biol.* 116:967–976 (1992).

Milner, J., et al., "p53 is associated with p34$^{cdc2}$ in transformed cells", *EMBO J.* 9:2885–2889 (1990).

Mirabito, P.M. et al., "BIMA, a TPR–containing Protein Required for Mitosis, Localizes to the Spindle Pole Body in *Aspergillus nidulans*", *J. Cell. Biol.* 120:959–968 (1993).

Münger, K., et al., "The E6 and E7 Genes of the Human Papillomavirus Type 16 Together Are Neccessary and Sufficient for Transformation of Primary Human Keratinocytes", *J. Virol.* 63:4417–4421 (1989).

Murray, A.W., et al., "The role of cyclin synthesis and degradation in the control of maturation promoting factor activity", *Nature* 339:280–286 (1989).

Nepveu, A., et al., "Alternative modes of c–myc regulation in growth factor–stimulated and differentiating cells", *Oncogene* 1:243–250 (1987).

Pines, J., et al., "Isolation of Human Cyclin cDNA: Evidence for Cyclin mRNA and Protein Regulation in the Cell Cycle and for interaction with p34$^{cdc2}$", *Cell* 58:833–846 (1989).

Rechsteiner, M., "Natural Substrates of the Ubiquitin Proteolytic Pathway", *Cell* 66:615–618 (1991).

Schärer, E., et al., "Mammalian p53 can function as a transcription factor in yeast", *Nuc. Acid. Res.* 20:1539–1545 (1992).

Scheffner, M., et al., "Targeted degradation of the retinoblastoma protein by human papillomavirus E7–E6 fusion proteins", *EMBO J.* 11:2425–2431 (1992).

Scheffner, M., et al., "Identification of a human ubiquitin–conjugating enzyme that mediates the E6–AP–dependent ubiquitination of p53", *Proc. Natl. Acad. Sci. USA* 91:8797–8801 (1994).

Schwartz, A.L., et al., "Immunoelectron microscopic localization of the ubiquitin–activating enzyme E1 in HepG2 cells", *Proc. Natl. Acad. Sci. USA* 89:5542–5546 (1992).

Seufert, W., et al., "Ubiquitin–conjugating enzymes UBC4 and UBC5 mediate selective degradation of short–lived and abnormal proteins", *EMBO J.* 9:543–550 (1990).

Seufert, W., et al., "Role of a ubiquitin–conjugating enzyme in degradation of S– and M–phase cyclins", *Nature* 373;78–81 (1995).

Tugendreich, S., et al., "Linking yeast genetics to mammalian genomes: Identificaton and mapping of the human homolog of CDC27 via the expressed sequence tag (EST) data base", *Proc. Natl. Acad. Sci. USA* 90:10031–10035 (1993).

Tyers, M., et al., "the Cln3–Cdc28 kinase complex of *S. cerevisiae* is regulated by proteolysis and phosphoryltaion", *EMBO J.* 11:1773–1784 (1992).

Vandré, D., "Distribution of cytoskeletal proteins sharing a conserved phosphorylated epitope", *Eur. J. Cell Biol.* 41:72–81 (1986).

Varshavsky, A., "The N–End Rule", *Cell* 69:725–735 (1992).

Watanabe, S., et al., "Human Papillomavirus Type 16 Transformation of Primary Human Embryonic Fibroblasts Requires Expression of Open Reading Frames E6 and E7", *J. Virol.* 63:965–969 (1989).

Zhen, M., "The *ubc-2* Gene of *Caenorhabditis elegans* Encodes a Ubiquitin–Conjugating Enzyme Involved in Selective Protein Degradation", *Mol. Cell. Biol.* 13:1371–1377 (1993).

Treier, M. et al., "Drosophila UbcD1 Encodes a Highly Conserved Ubiquitin–Conjugating Enzyme Involved in Selective Protein Degradation", *EMBO J.* 11:367–372, (1992).

King et al, Cell, 81, 279–288, 1995.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 1302 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1299

( x i ) SEQUENCE DESCRIPTION: SEQ ID NO:1:

| ATG | GCG | CTC | CGA | GTC | ACC | AGG | AAC | TCG | AAA | ATT | AAT | GCT | GAA | AAT | AAG | 48 |
|---|---|---|---|---|---|---|---|---|---|---|---|---|---|---|---|---|
| Met | Ala | Leu | Arg | Val | Thr | Arg | Asn | Ser | Lys | Ile | Asn | Ala | Glu | Asn | Lys | |
| 1 | | | | 5 | | | | | 10 | | | | | 15 | | |

| GCG | AAG | ATC | AAC | ATG | GCA | GGC | GCA | AAG | CGC | GTT | CCT | ACG | GCC | CCT | GCT | 96 |
|---|---|---|---|---|---|---|---|---|---|---|---|---|---|---|---|---|
| Ala | Lys | Ile | Asn | Met | Ala | Gly | Ala | Lys | Arg | Val | Pro | Thr | Ala | Pro | Ala | |
| | | | 20 | | | | | 25 | | | | | 30 | | | |

| GCA | ACC | TCC | AAG | CCC | GGA | CTG | AGG | CCA | AGA | ACA | GCT | CTT | GGG | GAC | ATT | 144 |
|---|---|---|---|---|---|---|---|---|---|---|---|---|---|---|---|---|
| Ala | Thr | Ser | Lys | Pro | Gly | Leu | Arg | Pro | Arg | Thr | Ala | Leu | Gly | Asp | Ile | |
| | | 35 | | | | | 40 | | | | | 45 | | | | |

| GGT | AAC | AAA | GTC | AGT | GAA | CAA | CTG | CAG | GCC | AAA | ATG | CCT | ATG | AAG | AAG | 192 |
|---|---|---|---|---|---|---|---|---|---|---|---|---|---|---|---|---|
| Gly | Asn | Lys | Val | Ser | Glu | Gln | Leu | Gln | Ala | Lys | Met | Pro | Met | Lys | Lys | |
| | 50 | | | | | 55 | | | | | 60 | | | | | |

| GAA | GCA | AAA | CCT | TCA | GCT | ACT | GGA | AAA | GTC | ATT | GAT | AAA | AAA | CTA | CCA | 240 |
|---|---|---|---|---|---|---|---|---|---|---|---|---|---|---|---|---|
| Glu | Ala | Lys | Pro | Ser | Ala | Thr | Gly | Lys | Val | Ile | Asp | Lys | Lys | Leu | Pro | |
| 65 | | | | | 70 | | | | | 75 | | | | | 80 | |

| AAA | CCT | CTT | GAA | AAG | GTA | CCT | ATG | CTG | GTG | CCA | GTG | CCA | GTG | TCT | GAG | 288 |
|---|---|---|---|---|---|---|---|---|---|---|---|---|---|---|---|---|
| Lys | Pro | Leu | Glu | Lys | Val | Pro | Met | Leu | Val | Pro | Val | Pro | Val | Ser | Glu | |
| | | | | 85 | | | | | 90 | | | | | 95 | | |

| CCA | GTG | CCA | GAG | CCA | GAA | CCT | GAG | CCA | GAA | CCT | GAG | CCT | GTT | AAA | GAA | 336 |
|---|---|---|---|---|---|---|---|---|---|---|---|---|---|---|---|---|
| Pro | Val | Pro | Glu | Pro | Glu | Pro | Glu | Pro | Glu | Pro | Glu | Pro | Val | Lys | Glu | |
| | | | 100 | | | | | 105 | | | | | 110 | | | |

| GAA | AAA | CTT | TCG | CCT | GAG | CCT | ATT | TTG | GTT | GAT | ACT | GCC | TCT | CCA | AGC | 384 |
|---|---|---|---|---|---|---|---|---|---|---|---|---|---|---|---|---|
| Glu | Lys | Leu | Ser | Pro | Glu | Pro | Ile | Leu | Val | Asp | Thr | Ala | Ser | Pro | Ser | |
| | | 115 | | | | | 120 | | | | | 125 | | | | |

| CCA | ATG | GAA | ACA | TCT | GGA | TGT | GCC | CCT | GCA | GAA | GAA | GAC | CTG | TGT | CAG | 432 |
|---|---|---|---|---|---|---|---|---|---|---|---|---|---|---|---|---|
| Pro | Met | Glu | Thr | Ser | Gly | Cys | Ala | Pro | Ala | Glu | Glu | Asp | Leu | Cys | Gln | |
| | 130 | | | | | 135 | | | | | 140 | | | | | |

| GCT | TTC | TCT | GAT | GTA | ATT | CTT | GCA | GTA | AAT | GAT | GTG | GAT | GCA | GAA | GAT | 480 |
|---|---|---|---|---|---|---|---|---|---|---|---|---|---|---|---|---|
| Ala | Phe | Ser | Asp | Val | Ile | Leu | Ala | Val | Asn | Asp | Val | Asp | Ala | Glu | Asp | |
| 145 | | | | | 150 | | | | | 155 | | | | | 160 | |

| GGA | GCT | GAT | CCA | AAC | CTT | TGT | AGT | GAA | TAT | GTG | AAA | GAT | ATT | TAT | GCT | 528 |
|---|---|---|---|---|---|---|---|---|---|---|---|---|---|---|---|---|
| Gly | Ala | Asp | Pro | Asn | Leu | Cys | Ser | Glu | Tyr | Val | Lys | Asp | Ile | Tyr | Ala | |
| | | | | 165 | | | | | 170 | | | | | 175 | | |

| TAT | CTG | AGA | CAA | CTT | GAG | GAA | GAG | CAA | GCA | GTC | AGA | CCA | AAA | TAC | CTA | 576 |
|---|---|---|---|---|---|---|---|---|---|---|---|---|---|---|---|---|
| Tyr | Leu | Arg | Gln | Leu | Glu | Glu | Glu | Gln | Ala | Val | Arg | Pro | Lys | Tyr | Leu | |
| | | | 180 | | | | | 185 | | | | | 190 | | | |

| CTG | GGT | CGG | GAA | GTC | ACT | GGA | AAC | ATG | AGA | GCC | ATC | CTA | ATT | GAC | TGG | 624 |
|---|---|---|---|---|---|---|---|---|---|---|---|---|---|---|---|---|
| Leu | Gly | Arg | Glu | Val | Thr | Gly | Asn | Met | Arg | Ala | Ile | Leu | Ile | Asp | Trp | |
| | | 195 | | | | | 200 | | | | | 205 | | | | |

| CTA | GTA | CAG | GTT | CAA | ATG | AAA | TTC | AGG | TTG | TTG | CAG | GAG | ACC | ATG | TAC | 672 |
|---|---|---|---|---|---|---|---|---|---|---|---|---|---|---|---|---|
| Leu | Val | Gln | Val | Gln | Met | Lys | Phe | Arg | Leu | Leu | Gln | Glu | Thr | Met | Tyr | |
| | | | 210 | | | | | 215 | | | | | 220 | | | |

```
ATG ACT GTC TCC ATT ATT GAT CGG TTC ATG CAG AAT AAT TGT GTG CCC        720
Met Thr Val Ser Ile Ile Asp Arg Phe Met Gln Asn Asn Cys Val Pro
225             230                 235                 240

AAG AAG ATG CTG CAG CTG GTT GGT GTC ACT GCC ATG TTT ATT GCA AGC        768
Lys Lys Met Leu Gln Leu Val Gly Val Thr Ala Met Phe Ile Ala Ser
                245                 250                 255

AAA TAT GAA GAA ATG TAC CCT CCA GAA ATT GGT GAC TTT GCT TTT GTG        816
Lys Tyr Glu Glu Met Tyr Pro Pro Glu Ile Gly Asp Phe Ala Phe Val
                260                 265                 270

ACT GAC AAC ACT TAT ACT AAG CAC CAA ATC AGA CAG ATG GAA ATG AAG        864
Thr Asp Asn Thr Tyr Thr Lys His Gln Ile Arg Gln Met Glu Met Lys
            275                 280                 285

ATT CTA AGA GCT TTA AAC TTT GGT CTG GGT CGG CCT CTA CCT TTG CAC        912
Ile Leu Arg Ala Leu Asn Phe Gly Leu Gly Arg Pro Leu Pro Leu His
        290                 295                 300

TTC CTT CGG AGA GCA TCT AAG ATT GGA GAG GTT GAT GTC GAG CAA CAT        960
Phe Leu Arg Arg Ala Ser Lys Ile Gly Glu Val Asp Val Glu Gln His
305                 310                 315                 320

ACT TTG GCC AAA TAC CTG ATG GAA CTA ACT ATC TTG GAC TAT GAC ATG       1008
Thr Leu Ala Lys Tyr Leu Met Glu Leu Thr Ile Leu Asp Tyr Asp Met
                325                 330                 335

GTG CAC TTT CCT CCT TCT CAA ATT GCA GCA GGA GCT TTT TGC TTA GCA       1056
Val His Phe Pro Pro Ser Gln Ile Ala Ala Gly Ala Phe Cys Leu Ala
                340                 345                 350

CTG AAA ATT CTG GAT AAT GGT GAA TGG ACA CCA ACT CTA CAA CAT TAC       1104
Leu Lys Ile Leu Asp Asn Gly Glu Trp Thr Pro Thr Leu Gln His Tyr
            355                 360                 365

CTG TCA TAT ACT GAA GAA TCT CTT CTT CCA GTT ATG CAG CAC CTG GCT       1152
Leu Ser Tyr Thr Glu Glu Ser Leu Leu Pro Val Met Gln His Leu Ala
        370                 375                 380

AAG AAT GTA GTC ATG GTA AAT CAA GGA CTT ACA AAG CAC ATG ACT GTC       1200
Lys Asn Val Val Met Val Asn Gln Gly Leu Thr Lys His Met Thr Val
385                 390                 395                 400

AAG AAC AAG TAT GCC ACA TCG AAG CAT GCT AAG ATC AGC ACT CTA CCA       1248
Lys Asn Lys Tyr Ala Thr Ser Lys His Ala Lys Ile Ser Thr Leu Pro
                405                 410                 415

CAG CTG AAT TCT GCA CTA GTT CAA GAT TTA GCC AAG GCT GTG GCA AAG       1296
Gln Leu Asn Ser Ala Leu Val Gln Asp Leu Ala Lys Ala Val Ala Lys
                420                 425                 430

GTG TAA                                                                1302
Val
```

( 2 ) INFORMATION FOR SEQ ID NO:2:

( i ) SEQUENCE CHARACTERISTICS:
        ( A ) LENGTH: 2472 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..2469

( x i ) SEQUENCE DESCRIPTION: SEQ ID NO:2:

```
ATG ACG GTG CTG CAG GAA CCC GTC CAG GCT GCT ATA TGG CAA GCA CTA         48
Met Thr Val Leu Gln Glu Pro Val Gln Ala Ala Ile Trp Gln Ala Leu
1               5                   10                  15

AAC CAC TAT GCT TAC CGA GAT GCG GTT TTC CTC GCA GAA CGC CTT TAT         96
Asn His Tyr Ala Tyr Arg Asp Ala Val Phe Leu Ala Glu Arg Leu Tyr
            20                  25                  30
```

-continued

| | | | | | | | | | | | | | | | | |
|---|---|---|---|---|---|---|---|---|---|---|---|---|---|---|---|---|
| GCA | GAA | GTA | CAC | TCA | GAA | GAA | GCC | TTG | TTT | TTA | CTG | GCA | ACC | TGT | TAT | 144 |
| Ala | Glu | Val 35 | His | Ser | Glu | Glu | Ala 40 | Leu | Phe | Leu | Leu | Ala 45 | Thr | Cys | Tyr | |
| TAC | CGC | TCA | GGA | AAG | GCA | TAT | AAA | GCA | TAT | AGA | CTC | TTG | AAA | GGA | CAC | 192 |
| Tyr | Arg 50 | Ser | Gly | Lys | Ala | Tyr 55 | Lys | Ala | Tyr | Arg | Leu 60 | Leu | Lys | Gly | His | |
| AGT | TGT | ACT | ACA | CCG | CAA | TGC | AAA | TAC | CTG | CTT | GCA | AAA | TGT | TGT | GTT | 240 |
| Ser 65 | Cys | Thr | Thr | Pro 70 | Gln | Cys | Lys | Tyr | Leu 75 | Leu | Ala | Lys | Cys | Cys | Val 80 | |
| GAT | CTC | AGC | AAG | CTT | GCA | GAA | GGG | GAA | CAA | ATC | TTA | TCT | GGT | GGA | GTG | 288 |
| Asp | Leu | Ser | Lys | Leu 85 | Ala | Glu | Gly | Glu | Gln 90 | Ile | Leu | Ser | Gly | Gly 95 | Val | |
| TTT | AAT | AAG | CAG | AAA | AGC | CAT | GAT | GAT | ATT | GTT | ACT | GAG | TTT | GGT | GAT | 336 |
| Phe | Asn | Lys | Gln 100 | Lys | Ser | His | Asp | Asp 105 | Ile | Val | Thr | Glu | Phe 110 | Gly | Asp | |
| TCA | GCT | TGC | TTT | ACT | CTT | TCA | TTG | TTG | GGA | CAT | GTA | TAT | TGC | AAG | ACA | 384 |
| Ser | Ala | Cys 115 | Phe | Thr | Leu | Ser | Leu 120 | Leu | Gly | His | Val | Tyr 125 | Cys | Lys | Thr | |
| GAT | CGG | CTT | GCC | AAA | GGA | TCA | GAA | TGT | TAC | CAA | AAG | AGC | CTT | AGT | TTA | 432 |
| Asp | Arg 130 | Leu | Ala | Lys | Gly | Ser 135 | Glu | Cys | Tyr | Gln | Lys 140 | Ser | Leu | Ser | Leu | |
| AAT | CCT | TTC | CTC | TGG | TCT | CCC | TTT | GAA | TCA | TTA | TGT | GAA | ATA | GGT | GAA | 480 |
| Asn 145 | Pro | Phe | Leu | Trp | Ser 150 | Pro | Phe | Glu | Ser | Leu 155 | Cys | Glu | Ile | Gly | Glu 160 | |
| AAG | CCA | GAT | CCT | GAC | CAA | ACA | TTT | AAA | TTC | ACA | TCT | TTA | CAG | AAC | TTT | 528 |
| Lys | Pro | Asp | Pro | Asp 165 | Gln | Thr | Phe | Lys | Phe 170 | Thr | Ser | Leu | Gln | Asn 175 | Phe | |
| AGC | AAC | TGT | CTG | CCC | AAC | TCT | TGC | ACA | ACA | CAA | GTA | CCT | AAT | CAT | AGT | 576 |
| Ser | Asn | Cys | Leu 180 | Pro | Asn | Ser | Cys | Thr 185 | Thr | Gln | Val | Pro | Asn 190 | His | Ser | |
| TTA | TCT | CAC | AGA | CAG | CCT | GAG | ACA | GTT | CTT | ACG | GAA | ACA | CCC | CAG | GAC | 624 |
| Leu | Ser | His 195 | Arg | Gln | Pro | Glu | Thr 200 | Val | Leu | Thr | Glu | Thr 205 | Pro | Gln | Asp | |
| ACA | ATT | GAA | TTA | AAC | AGA | TTG | AAT | TTA | GAA | TCT | TCC | AAT | TCA | AAG | TAC | 672 |
| Thr | Ile | Glu 210 | Leu | Asn | Arg | Leu | Asn 215 | Leu | Glu | Ser | Ser | Asn 220 | Ser | Lys | Tyr | |
| TCC | TTG | AAT | ACA | GAT | TCC | TCA | GTG | TCT | TAT | ATT | GAT | TCA | GCT | GTA | ATT | 720 |
| Ser 225 | Leu | Asn | Thr | Asp | Ser 230 | Ser | Val | Ser | Tyr | Ile 235 | Asp | Ser | Ala | Val | Ile 240 | |
| TCA | CCT | GAT | ACT | GTC | CCA | CTG | GGA | ACA | GGA | ACT | TCC | ATA | TTA | TCT | AAA | 768 |
| Ser | Pro | Asp | Thr | Val 245 | Pro | Leu | Gly | Thr | Gly 250 | Thr | Ser | Ile | Leu | Ser 255 | Lys | |
| CAG | GTT | CAA | AAT | AAA | CCA | AAA | ACT | GGT | CGA | AGT | TTA | TTA | GGA | GGA | CCA | 816 |
| Gln | Val | Gln | Asn 260 | Lys | Pro | Lys | Thr | Gly 265 | Arg | Ser | Leu | Leu | Gly 270 | Gly | Pro | |
| GCA | GCT | CTT | AGT | CCA | TTA | ACC | CCA | AGT | TTT | GGG | ATT | TTG | CCA | TTA | GAA | 864 |
| Ala | Ala | Leu 275 | Ser | Pro | Leu | Thr | Pro 280 | Ser | Phe | Gly | Ile | Leu 285 | Pro | Leu | Glu | |
| ACC | CCA | AGT | CCT | GGA | GAT | GGA | TCC | TAT | TTA | CAA | AAC | TAC | ACT | AAT | ACA | 912 |
| Thr | Pro 290 | Ser | Pro | Gly | Asp | Gly 295 | Ser | Tyr | Leu | Gln | Asn 300 | Tyr | Thr | Asn | Thr | |
| CCT | CCT | GTA | ATT | GAT | GTG | CCA | TCC | ACC | GGA | GCC | CCT | TCA | AAA | AAG | TCT | 960 |
| Pro 305 | Pro | Val | Ile | Asp | Val 310 | Pro | Ser | Thr | Gly | Ala 315 | Pro | Ser | Lys | Lys | Ser 320 | |
| GTT | GCC | AGA | ATC | GGC | CAA | ACT | GGA | ACA | AAG | TCT | GTC | TTC | TCA | CAG | AGT | 1008 |
| Val | Ala | Arg | Ile | Gly 325 | Gln | Thr | Gly | Thr | Lys 330 | Ser | Val | Phe | Ser | Gln 335 | Ser | |
| GGA | AAT | AGC | CGA | GAG | GTA | ACT | CCA | ATT | CTT | GCA | CAA | ACA | CAA | AGT | TCT | 1056 |
| Gly | Asn | Ser | Arg 340 | Glu | Val | Thr | Pro | Ile 345 | Leu | Ala | Gln | Thr | Gln 350 | Ser | Ser | |

| | | | | | | | | | | | | | | | | |
|---|---|---|---|---|---|---|---|---|---|---|---|---|---|---|---|---|
|GGT|CCA|CAA|ACA|AGT|ACA|ACA|CCT|CAG|GTA|TTG|AGC|CCC|ACT|ATT|ACA|1104|
|Gly|Pro|Gln|Thr|Ser|Thr|Thr|Pro|Gln|Val|Leu|Ser|Pro|Thr|Ile|Thr| |
| | |355| | | | |360| | | | |365| | | | |
|TCT|CCC|CCA|AAC|GCA|CTA|CCT|CGA|AGA|AGT|TCA|CGA|CTC|TTT|ACT|AGT|1152|
|Ser|Pro|Pro|Asn|Ala|Leu|Pro|Arg|Arg|Ser|Ser|Arg|Leu|Phe|Thr|Ser| |
| |370| | | | |375| | | | |380| | | | | |
|GAC|AGC|TCC|ACA|ACC|AAG|GAG|AAT|AGC|AAA|AAA|TTA|AAA|ATG|AAG|TTT|1200|
|Asp|Ser|Ser|Thr|Thr|Lys|Glu|Asn|Ser|Lys|Lys|Leu|Lys|Met|Lys|Phe| |
|385| | | | |390| | | | |395| | | | |400| |
|CCA|CCT|AAA|ATC|CCA|AAC|AGA|AAA|ACA|AAA|AGT|AAA|ACT|AAT|AAA|GGA|1248|
|Pro|Pro|Lys|Ile|Pro|Asn|Arg|Lys|Thr|Lys|Ser|Lys|Thr|Asn|Lys|Gly| |
| | | | |405| | | | |410| | | | |415| | |
|GGA|ATA|ACT|CAA|CCT|AAC|ATA|AAT|GAT|AGC|CTG|GAA|ATT|ACA|AAA|TTG|1296|
|Gly|Ile|Thr|Gln|Pro|Asn|Ile|Asn|Asp|Ser|Leu|Glu|Ile|Thr|Lys|Leu| |
| | | |420| | | | |425| | | | |430| | | |
|GAC|TCT|TCC|ATC|ATT|TCA|GAA|GGG|AAA|ATA|TCC|ACA|ATC|ACA|CCT|CAG|1344|
|Asp|Ser|Ser|Ile|Ile|Ser|Glu|Gly|Lys|Ile|Ser|Thr|Ile|Thr|Pro|Gln| |
| | |435| | | | |440| | | | |445| | | | |
|ATT|CAG|GCC|TTT|AAT|CTA|CAA|AAA|GCA|GCA|GCA|GGT|TTG|ATG|AGC|CTT|1392|
|Ile|Gln|Ala|Phe|Asn|Leu|Gln|Lys|Ala|Ala|Ala|Gly|Leu|Met|Ser|Leu| |
| |450| | | | |455| | | | |460| | | | | |
|CTT|CGT|GAA|ATG|GGG|AAA|GGT|TAT|TTA|GCT|TTG|TGT|TCA|TAC|AAC|TGC|1440|
|Leu|Arg|Glu|Met|Gly|Lys|Gly|Tyr|Leu|Ala|Leu|Cys|Ser|Tyr|Asn|Cys| |
|465| | | | |470| | | | |475| | | | |480| |
|AAA|GAA|GCT|ATA|AAT|ATT|TTG|AGC|CAT|CTA|CCT|TCT|CAC|CAC|TAC|AAT|1488|
|Lys|Glu|Ala|Ile|Asn|Ile|Leu|Ser|His|Leu|Pro|Ser|His|His|Tyr|Asn| |
| | | | |485| | | | |490| | | | |495| | |
|ACT|GGT|TGG|GTA|CTG|TGC|CAA|ATT|GGA|AGG|GCC|TAT|TTT|GAA|CTT|TCA|1536|
|Thr|Gly|Trp|Val|Leu|Cys|Gln|Ile|Gly|Arg|Ala|Tyr|Phe|Glu|Leu|Ser| |
| | | |500| | | | |505| | | | |510| | | |
|GAG|TAC|ATG|CAA|GCT|GAA|AGA|ATA|TTC|TCA|GAG|GTT|AGA|AGG|ATT|GAG|1584|
|Glu|Tyr|Met|Gln|Ala|Glu|Arg|Ile|Phe|Ser|Glu|Val|Arg|Arg|Ile|Glu| |
| | |515| | | | |520| | | | |525| | | | |
|AAT|TAT|AGA|GTT|GAA|GGC|ATG|GAG|ATC|TAC|TCT|ACA|ACA|CTT|TGG|CAT|1632|
|Asn|Tyr|Arg|Val|Glu|Gly|Met|Glu|Ile|Tyr|Ser|Thr|Thr|Leu|Trp|His| |
| |530| | | | |535| | | | |540| | | | | |
|CTT|CAA|AAA|GAT|GTT|GCT|CTT|TCA|GTT|CTG|TCA|AAA|GAC|TTA|ACA|GAC|1680|
|Leu|Gln|Lys|Asp|Val|Ala|Leu|Ser|Val|Leu|Ser|Lys|Asp|Leu|Thr|Asp| |
|545| | | | |550| | | | |555| | | | |560| |
|ATG|GAT|AAA|AAT|TCG|CCA|GAG|GCC|TGG|TGT|GCT|GCA|GGG|AAC|TGT|TTC|1728|
|Met|Asp|Lys|Asn|Ser|Pro|Glu|Ala|Trp|Cys|Ala|Ala|Gly|Asn|Cys|Phe| |
| | | | |565| | | | |570| | | | |575| | |
|AGT|CTG|CAA|CGG|GAA|CAT|GAT|ATT|GCA|ATT|AAA|TTC|TTC|CAG|AGA|GCT|1776|
|Ser|Leu|Gln|Arg|Glu|His|Asp|Ile|Ala|Ile|Lys|Phe|Phe|Gln|Arg|Ala| |
| | | |580| | | | |585| | | | |590| | | |
|ATC|CAA|GTT|GAT|CCA|AAT|TAC|GCT|TAT|GCC|TAT|ACT|CTA|TTA|GGG|CAT|1824|
|Ile|Gln|Val|Asp|Pro|Asn|Tyr|Ala|Tyr|Ala|Tyr|Thr|Leu|Leu|Gly|His| |
| | |595| | | | |600| | | | |605| | | | |
|GAG|TTT|GTC|TTA|ACT|GAA|GAA|TTG|GAC|AAA|GCA|TTA|GCT|TGT|TTT|CGA|1872|
|Glu|Phe|Val|Leu|Thr|Glu|Glu|Leu|Asp|Lys|Ala|Leu|Ala|Cys|Phe|Arg| |
| |610| | | | |615| | | | |620| | | | | |
|AAT|GCT|ATC|AGA|GTC|AAT|CCT|AGA|CAT|TAT|AAT|GCA|TGG|TAT|GGT|TTA|1920|
|Asn|Ala|Ile|Arg|Val|Asn|Pro|Arg|His|Tyr|Asn|Ala|Trp|Tyr|Gly|Leu| |
|625| | | | |630| | | | |635| | | | |640| |
|GGA|ATG|ATT|TAT|TAC|AAG|CAA|GAA|AAA|TTC|AGC|CTT|GCA|GAA|ATG|CAT|1968|
|Gly|Met|Ile|Tyr|Tyr|Lys|Gln|Glu|Lys|Phe|Ser|Leu|Ala|Glu|Met|His| |
| | | | |645| | | | |650| | | | |655| | |
|TTC|CAA|AAA|GCG|CTT|GAT|ATC|AAC|CCT|CAA|AGT|TCA|GTT|TTA|CTT|TGC|2016|
|Phe|Gln|Lys|Ala|Leu|Asp|Ile|Asn|Pro|Gln|Ser|Ser|Val|Leu|Leu|Cys| |
| | |660| | | | |665| | | | |670| | | | |

| | | | | | | | | | | | | | | | | |
|---|---|---|---|---|---|---|---|---|---|---|---|---|---|---|---|---|
| CAC | ATT | GGA | GTA | GTT | CAA | CAT | GCA | CTG | AAA | AAA | TCA | GAG | AAG | GCT | TTG | 2064 |
| His | Ile | Gly | Val | Val | Gln | His | Ala | Leu | Lys | Lys | Ser | Glu | Lys | Ala | Leu | |
| | | 675 | | | | 680 | | | | | | 685 | | | | |
| GAT | ACC | CTA | AAC | AAA | GCC | ATT | GTC | ATT | GAT | CCC | AAG | AAC | CCT | CTA | TGC | 2112 |
| Asp | Thr | Leu | Asn | Lys | Ala | Ile | Val | Ile | Asp | Pro | Lys | Asn | Pro | Leu | Cys | |
| | 690 | | | | | 695 | | | | 700 | | | | | | |
| AAA | TTT | CAC | AGA | GCC | TCA | GTT | TTA | TTT | CGA | AAT | GAA | AAA | TAT | AAG | TCT | 2160 |
| Lys | Phe | His | Arg | Ala | Ser | Val | Leu | Phe | Arg | Asn | Glu | Lys | Tyr | Lys | Ser | |
| 705 | | | | | 710 | | | | | 715 | | | | | 720 | |
| GCT | TTA | CAA | GAA | CTT | GAA | GAA | TTG | AAA | CAA | ATT | GTT | CCC | AAA | GAA | TCC | 2208 |
| Ala | Leu | Gln | Glu | Leu | Glu | Glu | Leu | Lys | Gln | Ile | Val | Pro | Lys | Glu | Ser | |
| | | | | 725 | | | | | 730 | | | | | 735 | | |
| CTC | GTT | TAC | TTC | TTA | ATA | GGA | AAG | GTT | TAC | AAG | AAG | TTA | GGT | CAA | ACG | 2256 |
| Leu | Val | Tyr | Phe | Leu | Ile | Gly | Lys | Val | Tyr | Lys | Lys | Leu | Gly | Gln | Thr | |
| | | | 740 | | | | | 745 | | | | | 750 | | | |
| CAC | CTC | GCC | CTG | ATG | AAT | TTC | TCT | TGG | GCT | ATG | GAT | TTA | GAT | CCT | AAA | 2304 |
| His | Leu | Ala | Leu | Met | Asn | Phe | Ser | Trp | Ala | Met | Asp | Leu | Asp | Pro | Lys | |
| | | 755 | | | | | 760 | | | | | 765 | | | | |
| GGA | GCC | AAT | AAC | CAG | ATT | AAA | GAG | GCA | ATT | GAT | AAG | CGT | TAT | CTT | CCA | 2352 |
| Gly | Ala | Asn | Asn | Gln | Ile | Lys | Glu | Ala | Ile | Asp | Lys | Arg | Tyr | Leu | Pro | |
| | 770 | | | | | 775 | | | | | 780 | | | | | |
| GAT | GAT | GAG | GAG | CCA | ATA | ACC | CAA | GAA | GAA | CAG | ATC | ATG | GGA | ACA | GAT | 2400 |
| Asp | Asp | Glu | Glu | Pro | Ile | Thr | Gln | Glu | Glu | Gln | Ile | Met | Gly | Thr | Asp | |
| 785 | | | | | 790 | | | | | 795 | | | | | 800 | |
| GAA | TCC | CAG | GAG | AGC | AGC | ATG | ACA | GAT | GCG | GAT | GAC | ACA | CAA | CTT | CAT | 2448 |
| Glu | Ser | Gln | Glu | Ser | Ser | Met | Thr | Asp | Ala | Asp | Asp | Thr | Gln | Leu | His | |
| | | | | 805 | | | | | 810 | | | | | 815 | | |
| GCA | GCT | GAA | AGT | GAT | GAA | TTT | TAA | | | | | | | | | 2472 |
| Ala | Ala | Glu | Ser | Asp | Glu | Phe | | | | | | | | | | |
| | | | 820 | | | | | | | | | | | | | |

( 2 ) INFORMATION FOR SEQ ID NO:3:

( i ) SEQUENCE CHARACTERISTICS:
        ( A ) LENGTH: 3176 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..3177

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | TCC | AGC | TCG | CCG | CTG | TCC | AAG | AAA | CGT | CGC | GTG | TCC | GGG | CCT | GAT | 48 |
| Met | Ser | Ser | Ser | Pro | Leu | Ser | Lys | Lys | Arg | Arg | Val | Ser | Gly | Pro | Asp | |
| 1 | | | | 5 | | | | | 10 | | | | | 15 | | |
| CCA | AAG | CCG | GGT | TCT | AAC | TGC | TCC | CCT | GCC | CAG | TCC | GTG | TTG | TCC | GAA | 96 |
| Pro | Lys | Pro | Gly | Ser | Asn | Cys | Ser | Pro | Ala | Gln | Ser | Val | Leu | Ser | Glu | |
| | | | 20 | | | | | 25 | | | | | 30 | | | |
| GTG | CCC | TCG | GTG | CCA | ACC | AAC | GGA | ATG | GCC | AAG | AAC | GGC | AGT | GAA | GCA | 144 |
| Val | Pro | Ser | Val | Pro | Thr | Asn | Gly | Met | Ala | Lys | Asn | Gly | Ser | Glu | Ala | |
| | | 35 | | | | | 40 | | | | | 45 | | | | |
| GAC | ATA | GAC | GAG | GGC | CTT | TAC | TCC | CGG | CAG | CTG | TAT | GTG | TTG | GGC | CAT | 192 |
| Asp | Ile | Asp | Glu | Gly | Leu | Tyr | Ser | Arg | Gln | Leu | Tyr | Val | Leu | Gly | His | |
| | 50 | | | | | 55 | | | | | 60 | | | | | |
| GAG | GCA | ATG | AAG | CGG | CTC | CAG | ACA | TCC | AGT | GTC | CTG | GTA | TCA | GGC | CTG | 240 |
| Glu | Ala | Met | Lys | Arg | Leu | Gln | Thr | Ser | Ser | Val | Leu | Val | Ser | Gly | Leu | |
| 65 | | | | | 70 | | | | | 75 | | | | | 80 | |
| CGG | GGC | CTG | GGC | GTG | GAG | ATC | GCT | AAG | AAC | ATC | ATC | CTT | GGT | GGG | GTC | 288 |
| Arg | Gly | Leu | Gly | Val | Glu | Ile | Ala | Lys | Asn | Ile | Ile | Leu | Gly | Gly | Val | |
| | | | | 85 | | | | | 90 | | | | | 95 | | |

```
AAG GCT GTT ACC CTA CAT GAC CAG GGC ACT GCC CAG TGG GCT GAT CTT      336
Lys Ala Val Thr Leu His Asp Gln Gly Thr Ala Gln Trp Ala Asp Leu
            100             105             110

TCC TCC CAG TTC TAC CTG CGG GAG GAG GAC ATC GGT AAA AAC CGG GCC      384
Ser Ser Gln Phe Tyr Leu Arg Glu Glu Asp Ile Gly Lys Asn Arg Ala
        115             120             125

GAG GTA TCA CAG CCC CGC CTC GCT GAG CTC AAC AGC TAT GTG CCT GTC      432
Glu Val Ser Gln Pro Arg Leu Ala Glu Leu Asn Ser Tyr Val Pro Val
    130             135             140

ACT GCC TAC ACT GGA CCC CTC GTT GAG GAC TTC CTT AGT GGT TTC CAG      480
Thr Ala Tyr Thr Gly Pro Leu Val Glu Asp Phe Leu Ser Gly Phe Gln
145             150             155             160

GTG GTG GTG CTC ACC AAC ACC CCC CTG GAG GAC CAG CTG CGA GTG GGT      528
Val Val Val Leu Thr Asn Thr Pro Leu Glu Asp Gln Leu Arg Val Gly
            165             170             175

GAG TTC TGT CAC AAC CGT GGC ATC AAG CTG GTG GTG GCA GAC ACG CGG      576
Glu Phe Cys His Asn Arg Gly Ile Lys Leu Val Val Ala Asp Thr Arg
        180             185             190

GGC CTG TTT GGG CAG CTC TTC TGT GAC TTT GGA GAG GAA ATG ATC CTC      624
Gly Leu Phe Gly Gln Leu Phe Cys Asp Phe Gly Glu Glu Met Ile Leu
    195             200             205

ACA GAT TCC AAT GGG GAG CAG CCA CTC AGT GCT ATG GTT TCT ATG GTT      672
Thr Asp Ser Asn Gly Glu Gln Pro Leu Ser Ala Met Val Ser Met Val
210             215             220

ACC AAG GAC AAC CCC GGT GTG GTT ACC TGC CTG GAT GAG GCC CGA CAC      720
Thr Lys Asp Asn Pro Gly Val Val Thr Cys Leu Asp Glu Ala Arg His
225             230             235             240

GGG TTT GAG AGC GGG GAC TTT GTC TCC TTT TCA GAA GTA CAG GGC ATG      768
Gly Phe Glu Ser Gly Asp Phe Val Ser Phe Ser Glu Val Gln Gly Met
            245             250             255

GTT GAA CTC AAC GGA AAT CAG CCC ATG GAG ATC AAA GTC CTG GGT CCT      816
Val Glu Leu Asn Gly Asn Gln Pro Met Glu Ile Lys Val Leu Gly Pro
        260             265             270

TAT ACC TTT AGC ATC TGT GAC ACC TCC AAC TTC TCC GAC TAC ATC CGT      864
Tyr Thr Phe Ser Ile Cys Asp Thr Ser Asn Phe Ser Asp Tyr Ile Arg
    275             280             285

GGA GGC ATC GTC AGT CAG GTC AAA GTA CCT AAG AAG ATT AGC TTT AAA      912
Gly Gly Ile Val Ser Gln Val Lys Val Pro Lys Lys Ile Ser Phe Lys
290             295             300

TCC TTG GTG GCC TCA CTG GCA GAA CCT GAC TTT GTG GTG ACG GAC TTC      960
Ser Leu Val Ala Ser Leu Ala Glu Pro Asp Phe Val Val Thr Asp Phe
305             310             315             320

GCC AAG TTT TCT CGC CCT GCC CAG CTG CAC ATT GGC TTC CAG GCC CTG     1008
Ala Lys Phe Ser Arg Pro Ala Gln Leu His Ile Gly Phe Gln Ala Leu
            325             330             335

CAC CAG TTC TGT GCT CAG CAT GGC CGG CCA CCT CGG CCC CGC AAT GAG     1056
His Gln Phe Cys Ala Gln His Gly Arg Pro Pro Arg Pro Arg Asn Glu
        340             345             350

GAG GAT GCA GCA GAA CTG GTA GCC TTA GCA CAG GCT GTG AAT GCT CGA     1104
Glu Asp Ala Ala Glu Leu Val Ala Leu Ala Gln Ala Val Asn Ala Arg
    355             360             365

GCC CTG CCA GCA GTG CAG CAA AAT AAC CTG GAC GAG GAC CTC ATC CGG     1152
Ala Leu Pro Ala Val Gln Gln Asn Asn Leu Asp Glu Asp Leu Ile Arg
370             375             380

AAG CTG GCA TAT GTG GCT GCT GGG GAT CTG GCA CCC ATA AAC GCC TTC     1200
Lys Leu Ala Tyr Val Ala Ala Gly Asp Leu Ala Pro Ile Asn Ala Phe
385             390             395             400

ATT GGG GGC CTG GCT GCC CAG GAA GTC ATG AAG GCC TGC TCC GGG AAG     1248
Ile Gly Gly Leu Ala Ala Gln Glu Val Met Lys Ala Cys Ser Gly Lys
            405             410             415
```

```
TTC ATG CCC ATC ATG CAG TGG CTA TAC TTT GAT GCC CTT GAG TGT CTC    1296
Phe Met Pro Ile Met Gln Trp Leu Tyr Phe Asp Ala Leu Glu Cys Leu
        420             425             430

CCT GAG GAC AAA GAG GTC CTC ACA GAG GAC AAG TGC CTC CAG CGC CAG    1344
Pro Glu Asp Lys Glu Val Leu Thr Glu Asp Lys Cys Leu Gln Arg Gln
            435             440             445

AAC CGT TAT GAC GGG CAA GTG GCT GTG TTT GGC TCA GAC CTG CAA GAG    1392
Asn Arg Tyr Asp Gly Gln Val Ala Val Phe Gly Ser Asp Leu Gln Glu
    450             455             460

AAG CTG GGC AAG CAG AAG TAT TTC CTG GTG GGT GCG GGG GCC ATT GGC    1440
Lys Leu Gly Lys Gln Lys Tyr Phe Leu Val Gly Ala Gly Ala Ile Gly
465             470             475             480

TGT GAG CTG CTC AAG AAC TTT GCC ATG ATT GGG CTG GGC TGC GGG GAG    1488
Cys Glu Leu Leu Lys Asn Phe Ala Met Ile Gly Leu Gly Cys Gly Glu
                485             490             495

GGT GGA GAA ATC ATC GTT ACA GAC ATG GAC ACC ATT GAG AAG TCA AAT    1536
Gly Gly Glu Ile Ile Val Thr Asp Met Asp Thr Ile Glu Lys Ser Asn
                500             505             510

CTG AAT CGA CAG TTT CTT TTC CGG CCC TGG GAT GTC ACG AAG TTA AAG    1584
Leu Asn Arg Gln Phe Leu Phe Arg Pro Trp Asp Val Thr Lys Leu Lys
            515             520             525

TCT GAC ACG GCT GCT GCA GCT GTG CGC CAA ATG AAT CCA CAT ATC CGG    1632
Ser Asp Thr Ala Ala Ala Ala Val Arg Gln Met Asn Pro His Ile Arg
530             535             540

GTG ACA AGC CAC CAG AAC CGT GTG GGT CCT GAC ACG GAG CGC ATC TAT    1680
Val Thr Ser His Gln Asn Arg Val Gly Pro Asp Thr Glu Arg Ile Tyr
545             550             555             560

GAT GAC GAT TTT TTC CAA AAC CTA GAT GGC GTG GCC AAT GCC CTG GAC    1728
Asp Asp Asp Phe Phe Gln Asn Leu Asp Gly Val Ala Asn Ala Leu Asp
                565             570             575

AAC GTG GAT GCC CGC ATG TAC ATG GAC CGC CGC TGT GTC TAC TAC CGG    1776
Asn Val Asp Ala Arg Met Tyr Met Asp Arg Arg Cys Val Tyr Tyr Arg
            580             585             590

AAG CCA CTG CTG GAG TCA GGC ACA CTG GGC ACC AAA GGC AAT GTG CAG    1824
Lys Pro Leu Leu Glu Ser Gly Thr Leu Gly Thr Lys Gly Asn Val Gln
        595             600             605

GTG GTG ATC CCC TTC CTG ACA GAG TCG TAC AGT TCC AGC CAG GAC CCA    1872
Val Val Ile Pro Phe Leu Thr Glu Ser Tyr Ser Ser Ser Gln Asp Pro
610             615             620

CCT GAG AAG TCC ATC CCC ATC TGT ACC CTG AAG AAC TTC CCT AAT GCC    1920
Pro Glu Lys Ser Ile Pro Ile Cys Thr Leu Lys Asn Phe Pro Asn Ala
625             630             635             640

ATC GAG CAC ACC CTG CAG TGG GCT CGG GAT GAG TTT GAA GGC CTC TTC    1968
Ile Glu His Thr Leu Gln Trp Ala Arg Asp Glu Phe Glu Gly Leu Phe
                645             650             655

AAG CAG CCA GCA GAA AAT GTC AAC CAG TAC CTC ACA GAC CCC AAG TTT    2016
Lys Gln Pro Ala Glu Asn Val Asn Gln Tyr Leu Thr Asp Pro Lys Phe
            660             665             670

GTG GAG CGA ACA CTG CGG CTG GCA GGC ACT CAG CCC TTG GAG GTG CTG    2064
Val Glu Arg Thr Leu Arg Leu Ala Gly Thr Gln Pro Leu Glu Val Leu
        675             680             685

GAG GCT GTG CAG CGC AGC CTG GTG CTG CAG CGA CCA CAG ACC TGG GCT    2112
Glu Ala Val Gln Arg Ser Leu Val Leu Gln Arg Pro Gln Thr Trp Ala
690             695             700

GAC TGC GTG ACC TGG GCC TGC CAC CAC TGG CAC ACC CAG TAC TCG AAC    2160
Asp Cys Val Thr Trp Ala Cys His His Trp His Thr Gln Tyr Ser Asn
705             710             715             720

AAC ATC CGG CAG CTG CTG CAC AAC TTC CCT CCT GAC CAG CTC ACA AGC    2208
Asn Ile Arg Gln Leu Leu His Asn Phe Pro Pro Asp Gln Leu Thr Ser
                725             730             735
```

```
                                                          -continued

TCA GGA GCG CCG TTC TGG TCT GGG CCC AAA CGC TGT CCA CAC CCG CTC              2256
Ser Gly Ala Pro Phe Trp Ser Gly Pro Lys Arg Cys Pro His Pro Leu
        740             745                 750

ACC TTT GAT GTC AAC AAT CCC CTG CAT CTG GAC TAT GTG ATG GCT GCT              2304
Thr Phe Asp Val Asn Asn Pro Leu His Leu Asp Tyr Val Met Ala Ala
        755             760                 765

GCC AAC CTG TTT GCC CAG ACC TAC GGG CTG ACA GGC TCT CAG GAC CGA              2352
Ala Asn Leu Phe Ala Gln Thr Tyr Gly Leu Thr Gly Ser Gln Asp Arg
        770             775                 780

GCT GCT GTG GCC ACA TTC CTG CAG TCT GTG CAG GTC CCC GAA TTC ACC              2400
Ala Ala Val Ala Thr Phe Leu Gln Ser Val Gln Val Pro Glu Phe Thr
785             790                 795                 800

CCC AAG TCT GGC GTC AAG ATC CAT GTT TCT GAC CAG GAG CTG CAG AGC              2448
Pro Lys Ser Gly Val Lys Ile His Val Ser Asp Gln Glu Leu Gln Ser
        805             810                 815

GCC AAT GCC TCT GTT GAT GAC AGT CGT CTA GAG GAG CTC AAA GCC ACT              2496
Ala Asn Ala Ser Val Asp Asp Ser Arg Leu Glu Glu Leu Lys Ala Thr
        820             825                 830

CTG CCC AGC CCA GAC AAG CTC CCT GGA TTC AAG ATG TAC CCC ATT GAC              2544
Leu Pro Ser Pro Asp Lys Leu Pro Gly Phe Lys Met Tyr Pro Ile Asp
        835             840                 845

TTT GAG AAG GAT GAT GAC AGC AAC TTT CAT ATG GAT TTC ATC GTG GCT              2592
Phe Glu Lys Asp Asp Asp Ser Asn Phe His Met Asp Phe Ile Val Ala
        850             855                 860

GCA TCC AAC CTC CGG GCA GAA AAC TAT GAC ATT CCT TCT GCA GAC CGG              2640
Ala Ser Asn Leu Arg Ala Glu Asn Tyr Asp Ile Pro Ser Ala Asp Arg
865             870                 875                 880

CAC AAG AGC AAG CTG ATT GCA GGG AAG ATC ATC CCA GCC ATT GCC ACG              2688
His Lys Ser Lys Leu Ile Ala Gly Lys Ile Ile Pro Ala Ile Ala Thr
        885             890                 895

ACC ACA GCA GCC GTG GTT GGC CTT GTG TGT CTG GAA CTG TAC AAG GTT              2736
Thr Thr Ala Ala Val Val Gly Leu Val Cys Leu Glu Leu Tyr Lys Val
        900             905                 910

GTG CAG GGG CAC CGA CAG CTT GAC TCC TAC AAG AAT GGT TTC CTC AAC              2784
Val Gln Gly His Arg Gln Leu Asp Ser Tyr Lys Asn Gly Phe Leu Asn
        915             920                 925

TTG GCC CTG CCT TTC TTT GGT TTC TCT GAA CCC CTT GCC GCA CCA CGT              2832
Leu Ala Leu Pro Phe Phe Gly Phe Ser Glu Pro Leu Ala Ala Pro Arg
        930             935                 940

CAC CAG TAC TAT AAC CAA GAG TGG ACA TTG TGG GAT CGC TTT GAG GTA              2880
His Gln Tyr Tyr Asn Gln Glu Trp Thr Leu Trp Asp Arg Phe Glu Val
945             950                 955                 960

CAA GGG CTG CAG CCT AAT GGT GAG GAG ATG ACC CTC AAA CAG TTC CTC              2928
Gln Gly Leu Gln Pro Asn Gly Glu Glu Met Thr Leu Lys Gln Phe Leu
                965             970                 975

GAC TAT TTT AAG ACA GAG CAC AAA TTA GAG ATC ACC ATG CTG TCC CAG              2976
Asp Tyr Phe Lys Thr Glu His Lys Leu Glu Ile Thr Met Leu Ser Gln
        980             985                 990

GGC GTG TCC ATG CTC TAT TCC TTC TTC ATG CCA GCT GCC AAG CTC AAG              3024
Gly Val Ser Met Leu Tyr Ser Phe Phe Met Pro Ala Ala Lys Leu Lys
        995             1000                1005

GAA CGG TTG GAT CAG CCG ATG ACA GAG ATT GTG AGC CGT GTG TCG AAG              3072
Glu Arg Leu Asp Gln Pro Met Thr Glu Ile Val Ser Arg Val Ser Lys
        1010            1015                1020

CGA AAG CTG GGC CGC CAC GTG CGG GCG CTG GTG CTT GAG CTG TGC TGT              3120
Arg Lys Leu Gly Arg His Val Arg Ala Leu Val Leu Glu Leu Cys Cys
1025            1030                1035                1040

AAC GAC GAG AGC GGC GAG GAT GTC GAG GTT CCC TAT GTC CGA TAC ACC              3168
Asn Asp Glu Ser Gly Glu Asp Val Glu Val Pro Tyr Val Arg Tyr Thr
        1045            1050                1055
```

```
ATC CGC TG                                                                                      3176
Ile Arg
```

( 2 ) INFORMATION FOR SEQ ID NO:4:

( i ) SEQUENCE CHARACTERISTICS:
        ( A ) LENGTH: 452 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..453

( x i ) SEQUENCE DESCRIPTION: SEQ ID NO:4:

```
CGG CAC GAG AGA ATC CAC AAG GAA TTG AAT GAT CTG GCA CGG GAC CCT         48
Arg His Glu Arg Ile His Lys Glu Leu Asn Asp Leu Ala Arg Asp Pro
 1               5                  10                  15

CCA GCA CAG TGT TCA GCA GGT CCT GTT GGA GAT GAT ATG TTC CAT TGG         96
Pro Ala Gln Cys Ser Ala Gly Pro Val Gly Asp Asp Met Phe His Trp
            20                  25                  30

CAA GCT ACA ATA ATG GGG CCA AAT GAC AGT CCC TAT CAG GGT GGA GTA        144
Gln Ala Thr Ile Met Gly Pro Asn Asp Ser Pro Tyr Gln Gly Gly Val
        35                  40                  45

TTT TTC TTG ACA ATT CAT TTC CCA ACA GAT TAC CCC TTC AAA CCA CCT        192
Phe Phe Leu Thr Ile His Phe Pro Thr Asp Tyr Pro Phe Lys Pro Pro
    50                  55                  60

AAG GTT GCA TTT ACA GTT GCA TTT ACC ACA AGA ATT TAT CAT CCA AAT        240
Lys Val Ala Phe Thr Val Ala Phe Thr Thr Arg Ile Tyr His Pro Asn
65                  70                  75                  80

ATT AAC AGT AAT GGC AGC ATT TGT CTT GAT ATT CTA CGA TCA CAG TGG        288
Ile Asn Ser Asn Gly Ser Ile Cys Leu Asp Ile Leu Arg Ser Gln Trp
                85                  90                  95

TCT CCA GCA CTA ACT ATT TCA AAA GTA CTC TTG TCC ATC TGT TCT CTG        336
Ser Pro Ala Leu Thr Ile Ser Lys Val Leu Leu Ser Ile Cys Ser Leu
           100                 105                 110

TTG TGT GAT CCC AAT CCA GAT GAT CCT TTA GTG CCT GAG ATT GCT CGG        384
Leu Cys Asp Pro Asn Pro Asp Asp Pro Leu Val Pro Glu Ile Ala Arg
       115                 120                 125

ATC TAC CAA ACA GAT AGA GAA AAG TAC AAC AGA ATA GCT CGG GAA TGG        432
Ile Tyr Gln Thr Asp Arg Glu Lys Tyr Asn Arg Ile Ala Arg Glu Trp
   130                 135                 140

ACT CAG AAG TAT GCG ATG TA                                             452
Thr Gln Lys Tyr Ala Met
145                 150
```

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GCGCGCAAGC TTATGTCCAG CTCGCCGCTG TCCAAG                                 36
```

( 2 ) INFORMATION FOR SEQ ID NO:6:

( i ) SEQUENCE CHARACTERISTICS:

```
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCGCGCGGAT CCTCAGCGGA TGGTGTATCG GACATA                                        36

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GCGCGCAAGC TTTAYGARGG WGGWGTYTTY TT                                            32

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCGCGCGAAT TCACNGCRTA YTTYTTNGTC CCAYTC                                        36

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GCGCGCAAGC TTCCNGTNGG NGAYTTRTTY CAYTGGCA                                      38

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCGCGCGAAT TCATNGTNAR NGCNGGCGAC CA                                            32

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear
```

(  i  i  ) MOLECULE TYPE: cDNA (  x  i  ) SEQUENCE DESCRIPTION: SEQ ID NO:11:

GCGCGCGGAT CCATGGCGCT CCGAGTC                                                                      2 7

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCGCGCCTTA AGCTACGTAC GGTGTC                                                                       2 6

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCGCGCGGAT CCATGACGGT GCTG                                                                         2 4

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GCGCGCTTCG AAAAATTCAT CACT                                                                         2 4

ASSAY AND REAGENTS FOR DETECTING INHIBITORS OF UBIQUITIN-DEPENDENT DEGRADATION OF CELL CYCLE REGULATORY PROTEINS

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. For instance, several key regulatory proteins are known to be degraded through the ubiquinin-mediated pathway, including certain transcriptional regulators, key enzymes of metabolic pathways, cyclins, and the tumor suppressor p53. One major function of the ubiquinin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation are covalently tagged with ubiquitin (Ub) through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process (for a review, see, e.g., Chiechanover, (1994) *Cell* 79:13–21). In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells. Therefore, it is an object of this invention to provide an assay for identifying inhibitors of ubiquitin-mediated degradation of such regulatory proteins. As described below, such inhibitors can ultimately be of therapeutic significance as anti-proliferative agents in the treatment of cancer, pathogenic infection, and even as immunosuppressants.

SUMMARY OF THE INVENTION

The present invention provides a systematic and practical approach for the identification of candidate agents able to inhibit ubiquitin-mediated degradation of a cell-cycle regulatory protein in cells from vertebrate organism, especially mammals, preferably humans. For instance, the assays permit identification of agents which inhibit ubiquitination of the cyclin proteins, e.g., B-type cyclins. One aspect of the present invention relates to a method for identifying an inhibitor of ubiquitin-mediated proteolysis of a cell-cycle regulatory protein by (i) providing a ubiquitin-conjugating system that includes the regulatory protein, a mitotic destruction complex (e.g., comprising CDC27 and CDC16), and ubiquitin under conditions which promote the ubiquitination of the target protein, and (ii) measuring the level of ubiquitination of the subject protein brought about by the system in the presence and absence of a candidate agent. A decrease in the level of ubiquitin conjugation is indicative of an inhibitory activity for the candidate agent. The level of ubiquitination of the regulatory protein can be measured by determining the actual concentration of protein:ubiquitin conjugates formed; or inferred by detecting some other quality of the subject protein affected by ubiquitination, including the proteolytic degradation of the protein. In certain embodiments, the present assay comprises an in vivo ubiquitin-conjugating system, such as a cell able to conduct the regulatory protein through at least a portion of a ubiquitin-mediated proteolytic pathway. In other embodiments, the present assay comprises an in vitro ubiquitin-conjugating system comprising a reconstituted protein mixture in which at least the ability to transfer ubiquitin to the regulatory protein is constituted.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning: A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M.P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and *Handbook Of Experimental Immunology*, Volumes I–IV (D. M. Weir and C. C. Blackwell, eds., 1986).

Other features and advantages of the invention will be apparent from the following detailed description, and from the claims.

DETAILED DESCRIPTION OF THE INVENTION

Figure 1:
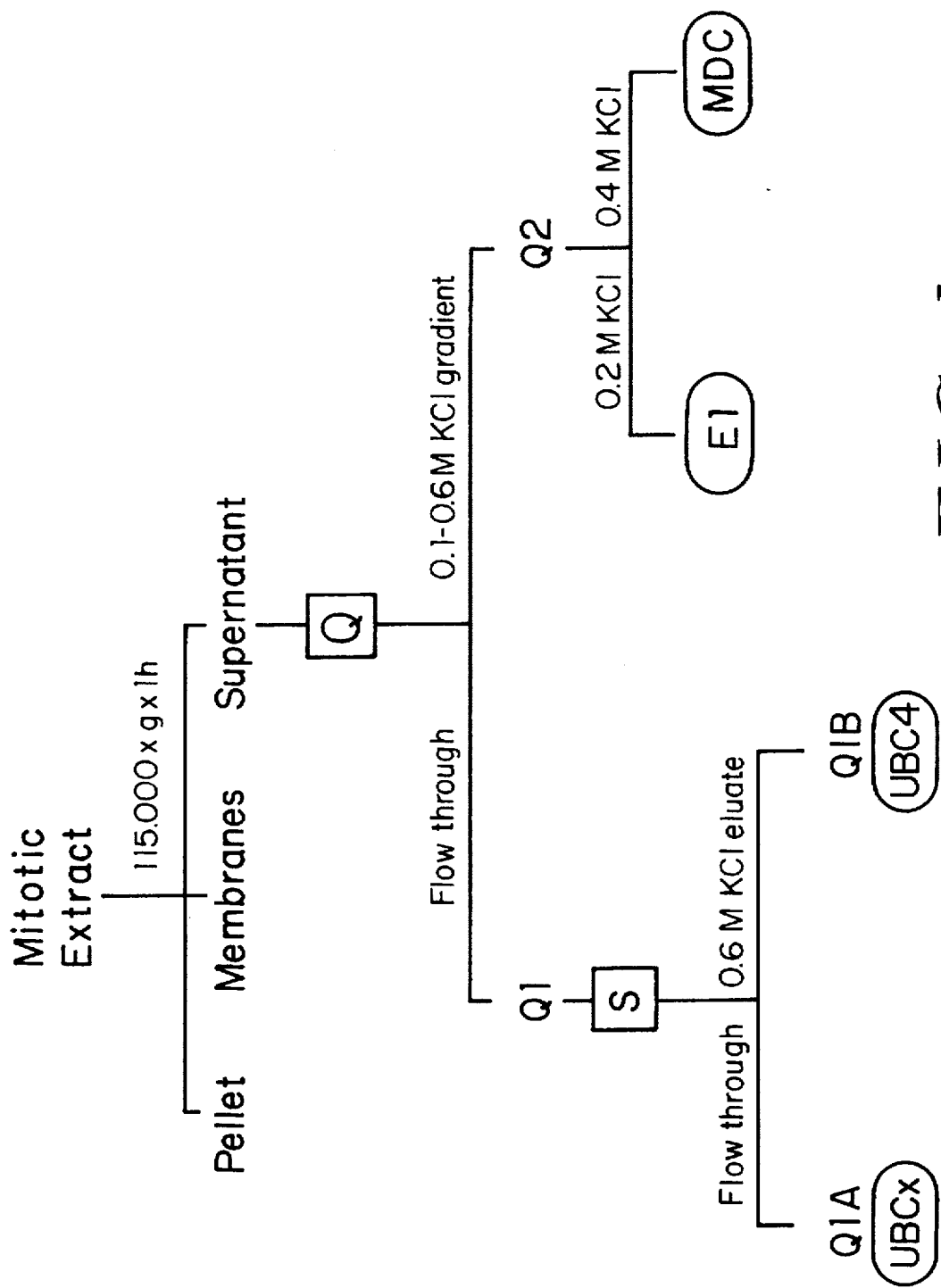
FIG. 1 is a scheme which shows the fractionation of Mitotic Xenopus egg extracts.

The ubiquitin system is essential for a wide spectrum of cellular phenomena, and is a component of many biological regulatory mechanisms, including aspects of growth control, metabolic regulation, embryonic development, and cell-cycle progression. The present invention makes available drug screening assays which provide a systematic and practical approach for the identification of candidate agents able to inhibit ubiquitin-mediated degradation of a cell-cycle regulatory protein, such as the regulatory cyclin proteins, in the cells of vertebrate organisms, e.g. mammals, e.g., humans.

In particular, the present invention is derived from the discovery that a "mitotic destruction complex" or "MDC", comprising the CDC27 and CDC16 proteins, is required in the cells of vertebrate organisms for ubiquitination of certain regulated proteins, which MDC functions with the apparent role of an E3. Accordingly, the subject assay, which can be used to identify agents that modulate MDC-dependent ubiquitination, comprises a ubiquitin-conjugating system that includes the regulatory protein, a CDC27 /CDC16 complex, and ubiquitin, and provides conditions which promote the ubiquitination of the target protein. The level of ubiquitination of the target protein brought about by the system is measured in the presence and absence of a candidate agent, wherein a statistically significant decrease in the level of ubiquitin conjugation indicates an inhibitory activity for the candidate agent. Likewise, an increase in the level of ubiquitination is indicative of a potentiating activity of the test agent. As described below, the level of ubiquitination of the regulatory protein can be measured by determining the actual concentration of target protein:ubiquitin conjugates formed; or inferred by detecting some other quality of the subject protein affected by ubiquitination, including the proteolytic degradation of the protein. In preferred embodiments, the present assay comprises an in vitro ubiquitin-conjugating system in which at least the ability to transfer ubiquitin to the regulatory protein is constituted.

As described herein, inhibitors of the ubiquitin-mediated proteolysis of the regulatory protein refer generally to those agents which may act anywhere along the ubiquitin degradation pathway; from the reaction steps leading up to an including conjugation of ubiquitin to the protein of interest, to the interaction and degradation of the ubiquitin conjugate by a proteosome complex. A subset of this class of inhibitors comprises the ubiquitination inhibitors, which include those agents that act at the level of preventing conjugation of ubiquitin to the subject protein, rather than at the steps of proteolytic degradation of the protein. As more fully illustrated below, this subset of inhibitors is directed more particularly to such steps as the activation of ubiquitin by E1, transfer of ubiquitin from E1 to E2, or transfer of the activated ubiquitin to the target regulatory protein from the E2:Ub conjugate via a CDC27/CDC16 complex. Likewise, protease inhibitors refer to that subset of inhibitors which act at the step of proteosome-catalyzed degradation of the regulatory protein:ubiquitin conjugate. Moreover, as will be clear from the following description, particular embodiments of the present assay can be chosen so as to discriminate between ubiquitination inhibitors and protease inhibitors.

For convience, certain terms employed in the specfication, examples, and appended claims are collected here.

The term "mitotic destruction complex" or "MDC" refers to a protein complex including a CDC27 protein and a CDC16 protein, which protein complex augments or otherwise facilitates the ubiquitination of a protein. In preferred embodiments, the MDC is a multi-protein complex which sediments by sucrose gradient centrifugation as an approximately 20S complex, e.g., in the range of 18S to 22S.

As used herein "MDC-dependent ubiquitination" refers to the conjugation of ubiquitin to a protein by a mechanism which requires the mitotic destruction complex for efficiency.

The term "target protein" refers to a protein, preferably a cellular protein, which can be ubiquitinated by an MDC-dependent reaction pathway.

The term "whole lysate" refers to a cell lysate which has not been manipulated, e.g. either fractionated, depleted or charged, beyond the step of merely lysing the cell to form the lysate. The term whole cell lysate does not, however, include lysates derived from cells which produce recombinant forms of one or more of the proteins required to constitute a ubiquitin-conjugating system for MDC-dependent ubiquitination of a target protein.

The term "charged lysate" refers to cell lysates which have been spiked with exogenous, e.g., purified, semi-purified and/or recombinant, forms of one or more components of an MDC-dependent ubiquitin-conjugating system, or the target protein thereof. The lysate can be charged after the whole cells have been harvested and lysed, or alternatively, by virtue of the cell from which the lysate is forms expressing a recombinant form of one or more of the conjugating system components.

The term "semi-purified cell extract" or, alternatively, "fractionated lysate", as used herein, refers to a cell lysate which has been treated so as to substantially remove at least one component of the whole cell lysate, or to substantially enrich at least one component of the whole cell lysate. "Substantially remove", as used herein, means to remove at least 10%, more preferably at least 50%, and still more preferably at least 80%, of the component of the whole cell lysate. "Substantially enrich", as used herein, means to enrich by at least 10%, more preferably by at least 30%, and still more preferably at least about 50%, at least one component of the whole cell lysate compared to another component of the whole cell lysate. The component which is removed or enriched can be a component of a ubiquitin-conjugation pathway, e.g., ubiquitin, a target protein, an E1, an E2, a CDC27, a CDC16, a cyclin, and the like, or it can be a component which can interfere with a ubiquitin-binding assay, e.g., a protease.

The term "semi-purified cell extract" is also intended to include the lysate from a cell, when the cell has been treated so as to have substantially more, or substantially less, of a given component than a control cell. For example, a cell which has been modified (by, e.g., recombinant DNA techniques) to produce none (or very little) of a component of a ubiquitin-conjugation pathway, will, upon cell lysis, yield a semi-purified cell extract.

The term "component of a ubiquitin-conjugation pathway", as used herein, refers to a component which can participate in the ubiquitination of a target protein either in vivo or in vitro. Exemplary components of a ubiquitin-conjugation pathway include ubiquitin, an E1, an E2, an E3, a CDC27/CDC 16 complex, a target protein, and the like. By "semi-purified", with respect to protein preparations, it is meant that the proteins have been previously separated from other cellular or viral proteins. For instance, in contrast to whole cell lysates, the proteins of reconstituted conjugation system, together with the target protein, can be present in the mixture to at least 50% purity relative to all other proteins in the mixture, more preferably are present at at least 75% purity, and even more preferably are present at 90–95% purity.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also refered to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

The term "gene" or "recombinant gene" refers to a nucleic acid comprising an open reading frame encoding a protein of the present invention, including both exon and (optionally) intron sequences. Exemplary recombinant genes encoding components of the subject ubiquitin conjugating systems include nucleic acids encoding CDC27, CDC16, ubiquitin conjugating enzymes, such as UBC4 or UBC5, and ubiquitin.

The term "recombinant protein" refers to a protein of the present ubiquitin conjugating systems which is produced by recombinant DNA techniques, wherein generally DNA encoding, for example, an E2 enzyme, a component of the MDC, or a target protein, is inserted into a suitable expression vector which is in turn used to transform a host cell to produce the heterologous protein.

As used herein, the term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a protein of the present ubiquitin conjugating systems.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors" . In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the proteins of the subject ubiquitination assays with a second amino acid sequence defining a domain foreign to and not substantially homologous with any domain of the first protein. A chimeric protein may present a foreign domain which is found (albeit in a different protein) in an organism which also expresses the first protein, or it may be an "interspecies", "intergeneric", etc. fusion of protein structures expressed by different kinds of organisms. An exemplary fusion protein is a cyclin B/glutathione-s-transferase fusion protein.

I. Target Proteins

In a preferred,embodiment, the target protein is a cyclin, particularly a cyclin having a cyclin destruction box, e.g., a B-type cyclin. In general, cyclin degradation is a key step governing exit from mitosis and progression into the next cell-cycle. For example, the transition from metaphase to anaphase, which marks the end of mitosis, is induced by the degradation of cyclin B by a ubiquitin-mediated pathway, which in turn leads to the inactivation of cyclin-dependent kinases (cdk) operational at that cell-cycle stage. As cells enter interphase, cyclin degradation ceases, cyclin accumulates and, as a result of a complex series of post-translational modifications, cyclin B/cdk complexes are activated as kinases which drive the cell through mitosis. Cyclin B degradation is thus one of the crucial events in exiting mitosis (see, e.g., King et al. (1994) Cell 79:563). Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E, F, G or H) can be used as antiproliferative agents.

The N-termini of mitotic cyclins contain a short conserved sequence, called the destruction box, that is required for their degradation (Glotzer et al. (1991) *Nature* 349:132). The cyclin ubiquitination reaction is unusual in that it is specified at two levels: substrate recognition which is reflected in the requirement for an intact destruction box, and temporal control in the limitation of its activity to a specific phase of the cell cycle, late mitosis and early G1 (see, e.g., Amon et al., (1994) *Cell* 77:1037).

In other embodiments of the subject assay, the target regulatory protein is the tumor suppressor p53, and the assay is used to identify inhibitors of ubiquitin-mediated destruction of p53. Many lines of evidence point to the importance of p53 in human carcinogenesis. For instance, mutations within the p53 gene are the most frequent genetic aberration thus far associated with human cancer. Under normal condition p53 is an unstable protein and is present at very low levels in the cell, and the level of p53 in a cell appears to be controlled at least in party by degradation involving the ubiquitin system. Treating cells with UV light or X rays dramatically reduces the rate of p53 degradation, leading to a rapid increase in its concentration in the cell and presumably inducing the transcription of genes that block passage through the restriction point. However, while normal cell lines irradiated in G1 fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. An inhibitor developed using the subject assay could be used therapeutically to enhance the function of the p53 checkpoint by increasing the steady state concentration of p53 in the treated cell. The anti-proliferative activity of such an inhibitor can be employed in the treatment of hyperplasias or neoplasias by increasing the fortitude of the checkpoint in transformed cells which contain wild-type p53 (i.e. can induce apoptosis in cells overexpressing c-myc), or by offsetting a diminishment in p53 activity by increasing the level of (mutant) p53. Moreover, such agents can also be used prophylactically to increase p53 levels and thereby enhance the protection against DNA damaging agents when it is known that exposere to damaging agents, such as radiation, is imminent.

In yet another embodiment, the targeted regulatory protein is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. The myc protein has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:148). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur even in the absence of a second cytotoxic drug.

Still another target protein which may undergo MDC-mediated ubiquitination is the AP1 component, c-fos. The fos oncogene product, which can undergo ubiquitin-mediated degradation in a cell, has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to oncogenesis. Given the prominence of c-fos as an early response gone, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

II. Ubiquitin Conjugating Reactions

Assays which approximate the ubiquitination of target regulatory proteins in vertebrate cells, particularly mammalian cells, can be generated in many different forms, and include assays based on cell-free systems, e.g. purified proteins or cell lysates, as well as cell-based assays which utilize intact cells. Assays as described herein can be used in conjunction with the subject MDC complexes to generate a ubiquitin-conjugating system for detecting agents able to inhibit particular MDC-dependent ubiquitination of cellular or viral regulatory proteins. Such inhibitors can be used, for example, in the treatment of proliferative and/or differentiative disorders, to modulate apoptosis, and in the treatment of viral infections.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential inhibitors of MDC-dependent ubiquitination of a target protein can be detected in a cell-free assay generated by consitution of a functional ubiquitin conjugating system (including a CDC27 /CDC16 complex) in a cell lysate, such as generated by charging a ubiquitin-depleted reticulocyte lysate (Hershko et al. (1983) *J Biol Chem* 258:8206–6214) with one or more of a ubiquitin-conjugating enzyme, an E1 enzyme, a mitotic destruction complex, ubiquitin, and/or a substrate for MDC-dependent ubiquitination, such as a B-type cyclin. In an alternate format, the assay can be derived as a reconstituted protein mixture which, as described below, offers a number of benefits over lysate-based assays.

In an illustrative embodiment of the present assay, the ubiquitin-conjugating system comprises a reconstituted protein mixture of at least semi-purified proteins, and even more preferably of purified proteins. The reconstituted protein mixture is derived from preparations of the regulatory protein and ubiquitin under conditions which drive the conjugation of the two molecules. For instance, the mixture can include a ubiquitin-activating enzyme (E1), a ubiquitin-conjugating enzyme (E2), an MDC comprising CDC27 and CDC16, and a nucleotide triphosphate (e.g. ATP). Alternatively, the E1 enzyme, the ubiquitin, and the nucleotide triphosphate can be substituted in the system with a pre-activated ubiquitin in the form of an E1:Ub conjugate. Likewise, a pre-activated ubiquitin can instead comprise an E2:Ub conjugate.

In preferred embodiments, the purified protein mixture substantially lacks any proteolytic activity which would degrade the target protein and/or components of the ubiquitin conjugating system. For instance, the reconstituted system can be generated to have less than 10% of the proteolytic activity associated with a typical reticulocyte lysate, and preferably no more than 5%, and most preferably less than 2%. Alternatively, the mixture can be generated to include, either from the onset of ubiquitination or from some point after ubiquitin conjugation of the regulatory protein, a ubiquitin-dependent proteolytic activity, such as a purified proteosome complex, that is present in the mixture at measured amounts.

In general, the use of reconstituted protein mixtures will be preferred among cell-free embodiments of the subject assay because they allow more careful control of the reaction conditions in the ubiquitin-conjugating system. Moreover, the system can be derived to favor discovery of inhibitors of particular steps of the ubiquitination process, especially the MDC-dependent steps. For instance, as set out above, a reconstituted protein assay can be generated which does not facilitate degradation of the ubiquitinated protein, and which utilizes a precharged E2:Ub conjugate. The level of ubiquitin-conjugated protein, which is dependent on a CDC27/CDC16 complex can easily be measured directly in such as system, both in the presence and absence of a candidate agent, thereby enhancing the ability to detect an inhibitor of the CDC27/CDC 16-dependent step. Alternatively, the Ub-conjugating system can be allowed to develop a steady state level of regulatory protein:Ub conjugates in the absence of a proteolytic activity, but then shifted to a degradative system by addition of purified Ub-dependent proteases. Such degradative systems would be amenable to identifying proteosome inhibitors.

Moreover, in the subject method, ubiquitin conjugating systems derived from purified proteins hold a number of significant advantages over cell lysate or wheat germ extract based assays (collectively referred to hereinafter as "lysates"), especially "whole" lysates. Unlike the reconstituted protein system, the synthesis and destruction of the target protein cannot be readily controlled for in lysate-based assays. Without knowledge of particular kinetic parameters for Ub-independant and Ub-dependent degradation of the target protein in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the target protein, as such lysates may continue to synthesize the protein during the assay, and will do so at unpredictable rates.

Accordingly, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the target protein itself has a relatively short half-life, especially if due to degradative processes other than the ubiquitin-mediated pathway to which an inhibitor is sought. However, as described, this effect can be mitigated by the use of protease inhibitors such as PMSF or TPCK to inhibit proteolysis of the target protein, though broad-spectrum inhibitors will knock out both ubiquitin-dependent and independent proteolysis.

Moreover, many of the disadvantages of whole cell lysates described above can be overcome by the use of semi-purified cell extracts and/or lysates that have been charged with one or more components of a ubiquitin-conjugation pathway. For example, by selective removal of cell lysate components which interfere with ubiquitination assays, an assay may be feasible in a cell extract even without further purification. Such an approach makes possible rapid and inexpensive development of assay systems suitable for use with ubiquitination assays.

Thus, in another aspect of the subject invention, the ubiquitin-conjugating system comprises a semi-purified cell extract. For instance, as described in the examples below, semi-purified cell extracts can be produced by treatment of cell lysates by a variety of techniques. For example, chromatographic methods and the like can be used to partially purify at least one component of the cell lysate. Likewise, semi-purified cell lysates may be prepared by treatment of a cell lysate to selectively remove a component of the lysate, for example, by immunoprecipitation (see, e.g., Example 6, infra). Many other methods for the preparation of semi-purified cell extracts by the selective removal or enrichment of components of a cell lysate will be evident to the skilled artisan.

In yet another embodiment of the subject assay, a cell lysate can be charged with certain of the components of an MDC-dependent ubiquitination system. For example, in addition to inhibitors or potentiators of ubiquitination, a semi-purified cell extract can be charged with UBC4, UBC5, CDC27, CDC16, cyclin B and the like. Likewise, lysates can be generated from cells recombinantly manipulated to produce, for example, a labeled component to the assay, such as a myc-labeled ubiquitin or a GST-cyclin fusion protein.

Ubiquitination of the target regulatory protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated target protein assessed, using standard electrophoresis protocols, e.g., by detecting an increase in molecular weight of the target protein that corresponds to the addition of one or more ubiquitin chains. For example, one or both of the target protein and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the regulatory protein, including immunoblot analysis using antibodies specific for either the regulatory protein or ubiquitin, or derivatives thereof. As described below, the antibody can be replaced with another molecule able to bind one of either the regulatory protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the regulatory protein and ubiquitin conjugates in the gel by standard staining protocols, including coomassie blue and silver staining.

In another embodiment, an immunoassay or similar binding assay, is used to detect and quantify the level of ubiquitinated regulatory protein produced in the ubiqutin-conjugating system. Many different immunoassay techniques are amenable for such use can be employed to detect and quantitate the regulatory protein:Ub conjugates. For example, the wells of a microtitre plate (or other suitable solid phase) can be coated with an antibody which specifically binds one of either the regulatory protein or ubiquitin. After incubation of the ubiquitin-conjugated system with and without the candidate agent, the products are contacted with the matrix bound antibody, unbound material removed by washing, and ubiquitin conjugates of the regulatory protein specifically detected. To illustrate if an antibody which binds the regulatory protein is used to sequester the protein on the matrix, then a detectable anti-ubiquitin antibody can be used to score for the presence of ubiquitinated regulatory protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the regulatory protein or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of regulatory protein (bound to the matrix via a conjugated ubiquitin moiety) is detected in each well. Alternatively, the microtitre plate wells can be coated with an antibody (or other binding molecule) which binds and squesters the regulatory protein on the solid support, and detection of ubiquitinated conjugates of the matrix-bound regulatory protein are subsequently carried out using a detectable streptavidin derivative, such as an alkaline phosphatase/streptavidin complex.

In similar fashion, epitope-tagged ubiquitin, such as myc-ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-medicated proteolysis of the conjugated regulatory protein.

Other ubiquitin derivatives include detectable labels which do not interfere greatly with the conjugation of ubiquitin to the regulatory protein. Such detectable labels can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the regulatory protein. For example, the regulatory protein can be genenrated as a glutathione-S-transferase (GST) fusion protein. As a practical matter, such GST fusion protein can enable easy purification of the regulatory protein in the preparation of components of the ubiquitin-conjugating system (see, for example, *Current Protocols in Molecular Biology*, eds. Ausubel et al, (NY: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the regulatory protein from the ubiguitin-conjugating system, and the level of ubiquitin immobilized can be measured as described. Likewise, where the matrix is generated to bind ubiquitin, the level of sequestestered GST-regulatory protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the regulatory protein and an enzymatic activity are contemplated by the present method. For example, fusion proteins containing β-galactosidase or luciferase, to name but a few, can be employed as labels to determine the amount of regulatory protein sequestered on a matrix by virtue of a conjugated ubiquitin chain.

Moreover, such enzymatic fusion proteins can be used to detect and quantitate ubiquitinated regulatory protein in a heterogeneous assay, e.g., one which does not require separation of the components of the conjugating system. For example, ubiquitin conjugating systems can be generated to have a ubiquitin-dependent protease which degrades the regulatory protein. The enzymatic activity of undegraded fusion protein provides a detectable signal, in the presence of substrate, for effectively measuring the level of the regulatory protein ubiquitination. Similarly, in a non-degradative conjugating system, ubiquitintation of the regulatory protein portion of the fusion protein can allosterically influence the enzymatic activity associated with the fusion the protein and thereby provides a means for monitoring the level of ubiquitin conjugation.

In binding assay-type detection steps such as set out above, the choice of which of either the regulatory protein or ubiquitin should be specifically sequestered on the matrix will depend on a number of factors, including the relative abundance of both components in the conjugating system. For instance, where the reaction conditions of the ubiquitin cojugating system provide ubiquitin at a concentration far in excess of the level of the regulatory protein, (e.g., one order of magnitude or greater) sequestering the ubiquitin and detecting the amount of regulatory protein bound with the ubiquitin can provide less dynamic range to the detection step of the present method than the converse embodiment of sequestering the regulatory protein and detecting ubiquitin conjugates from the total regulatory protein bound to the matrix. That is, where ubiquitin is provided in great excess relative to the regulatory protein, the percentage of ubiquitin conjugated regulatory protein in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound regulatory protein. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

In still further embodiments of the present invention, the ubiquitin-conjugating system is generated in whole cells, taking advantage of cell culture techniques to support the subject assay. For example, as described below, the ubiquitin-conjugating system (including the target protein and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the ageembto gain entry into the cell. Furthermore, certain of the in vivo embodiments of the assay, such as examples given below, are amenable to high through-put analysis of candidate agents.

The components of the ubiquitin-conjugating system, including the regulatory protein, can be endogenous to the cell selected to support the assay. Alternatively, some or all of the components can be derived from exogenous sources. For instance, a recombinantly produced E2 enzyme, such as UBC4, or recombinantly produced components of an MDC, such as CDC27, can be expressed in the cell by recombinant techniques (such as through the use of an expression vector), as well as by microinjecting the proteins themselves or mRNA encoding the protein.

In any case, the cell is ultimately manipulated after incubation with a candidate inhibitor in order to facilitate detection of ubiquitination or ubiquitin-mediated degradation of the regulatory protein. As described above for assays performed in reconstituted protein mixtures or lysates, the effectiveness of a candidate inhibitor can be assessed by measuring direct characteristics of the regulatory protein, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate.

Indirect measurement of ubiquitination of the target protein can also be accomplished by detecting a biological activity associated with the regulatory protein that is either attenuated by ubiquitin-conjugation or destroyed along with the regulatory protein by ubiquitin-dependent proteolytic processes. As set out above, the use of fusion proteins comprising the regulatory protein and an enzymatic activity are representative embodiments of the subject assay in which the detection means relies on indirect measurement of ubiquitination of the regulatory protein by quantitating an associated enzymatic activity.

Where the regulatory protein has a relatively short half-life due to ubiquitin-dependent or independent degradation in the cell, preferred embodiments of the assay either do not require cell lysis, or, alternatively, generate a longer lived detection signal that is independent of the regulatory protein's fate after lysis of the cell. With respect to the latter embodiment, the detection means can comprise, for example, a reporter gene construct which includes a positive transcriptional regulatory element that binds and is responsive to the regulatory protein. For instance, where the regulatory protein of interest ips 53, p53 responsive elements can be used to construct the reporter gene producing a gene product which is a detectable label, such as luciferase or β-galactosidase (see, for example, U.S. Pat. No. 5,362, 623), and which is produced in the intact cell. The label can be measured in a subsequent lysate of the cell. However, the lysis step is preferably avoided, and providing a step of lysing the cell to measure the label will typically only be employed where detection of the label cannot be accomplished in whole cells.

Where the regulatory protein does not itself posses DNA-binding ability, can be arranged as part of an interaction trap assay designed for detecting inhibitors of the MDC-dependent destruction of the protein (see, for example, U.S. Pat. No. 5,283,317; PCT publication WO94/10300; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696) In an illustrative embodiment, Saccharomyces cgrevisiae YPB2 cells are transformed simultaneously with a plasmid encoding a GAL4db-CDC2 (where CDC2 is a human CDC2) fusion and with a plasmid encoding the GAL4ad domain fused to human cyclin B. Moreover, the strain is transformed such that the GAL4-responsive promoter drives expression of a phenotypic marker. For example, the ability to grow in the absence of histidine depends on the expression of the HIS3 gene if it is under control of a GAL4-responsive promoter and, therefore, indicates that a functional GAL4 activator has been reconstituted through the interaction of the human CDC2 and cyclin B fusion protiens. The strain is further manipulated to be "humanized" with respect to MDC-mediated ubiquitination of the cyclin B fusion protein. For example, conditional inactivation of the yeast UBC4, with concomitant expression of the human UBC4 enzyme, or alternatively, replacement of the yeast CDC27 and/or CDC16 genes with the human homologs, provides a humanized system whereby the cyclin B fusion protein can be ubiquitinated by a mechanism which approximate the MDC-dependent ubiquitination which occurs in vertebrate cells.

Thus, agents able to inhibit the ubiquitination of the cyclin B fusion protein will result in yeast cells able to growth in the absence of histidine, as the GAL4db-CDC2 and GAL4ad-cyclin fusion proteins will be able to interact and cause expression of the HIS3 gene. Alternatively, the agents which do not effect the ubiquitination of the cyclin B fusion protein will result in cells unable to grow in the absence of histidine as the GAL4ad-cyclin fusion protein will be degraded or otherwise prevented from interacting with the GAL4-CDC2 protein.

III. Competitive binding assays

Furthermore, drug screening assays can be generated which do not measure ubiquitination per se, but rather detect inhibitory agents on the basis of their ability to interfere with binding of one of the proteins involved in the MDC-dependent ubiquitin conjugation pathway. In an exemplary binding assay, the compound of interest is contacted with a mixture generated from an isolated and purified E2 protein, such as UBC4 and an mitotic destruction complex, such as comprising the CDC27 and CDC16 proteins Alternatively, the MDC and cyclin are combined in the presence and absence of test agents so as to provide a competitive binding assay which detects agents able to compete with the cyclin for binding to the MDC. Detection and quantification of complexes between the MDC and either UBC4 or the cyclin provides a means for determining the compound's efficacy at inhibiting (or potentiating) complex formation between the MDC and other components of the MDC-dependent ubiquitin pathway. The efficacy of the compound can be assesed by generating dose response curves from data obtained using various concentrations of the test compound. Moreover, a control assay can also be performed to provide a baseline for comparison. In the control assay, isolated and purified UBC4 or cyclin is added to a composition containing the MDC, and the formation of complexes is quantitate in the absence of the test compound.

Complex formation between the E2 protein or regulatory protein and the MDC may be detected by a variety of techniques, many of which are effectively described above. For instance, modulation in the formation of complexes can be quantitated using, for example, detectably labeled proteins (e.g. radiolabelled, fluorescently labelled, or enzymatically labelled), by immunoassay, or by chromatographic detection.

Typically, it will be desirable to immobilize either the E2, the regulatory protein or a component of the MDC, such as the CDC27 protein, to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST/cyclin fusion proteins can be adsorbed onto glutathione sepharose beads (Sigma Chemical, St. Louis, Mo.) or glutathione derivatized microtitre plates, which are then combined with the MDC, e.g. containing $^{35}$S-labeled proteins, and the test compound and incubated under conditions conducive to complex formation. Following incubation, the beads are washed to remove any unbound MDC, and the matrix bead-bound radiolabel determined directly (e.g. beads placed in scintilant), or in the superntantant after the complexes are dissociated, e.g. when microtitre plaste is used. Alternatively, after washing away unbound protein, the complexes can be dissociated from the matrix, separated by SDS-PAGE gel, and the level of, for example, CDC27 or CDC16 protein found in the matrix-bound fraction quantitated from the gel using standard electrophoretic techniques.

In similar fashion, the interaction trap described above can be provided to detect agents able to modulate the binding of CDC27 or CDC 16 or another component of the MDC to an E2 or a regulatory protein.

With respect to sources for the proteins constituting the ubiquitin-conjugating system and competitive binding assays, particularly those used to generate the reconstituted protein mixture or other embodiments requiring recombinant or purifed preparations of proteins, many species of the enzymes and other proteins involved in ubiquitination have been identified, and in a significant number of instances, have been cloned so that recombinant sources exist. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-sepharase) in the presence of ATP. As described in Example 1, such a protocol can be used to purify recombinantly expressed E1. Moreover, E1 enzymes bound to the immobilized ubiquitin can be exchanged with E2 enzymes, such as UBC4. Thus, both E1 and E2 enzymes can be specifically purified on such columns, and can be recovered after elution with, for example, dithiothreitol. Under appropriate elution conditions, ubiquitin activated E1 or E2 complexes can be isolated and, as described herein, used in the present assay to increase the selectivity of the assay for an inhibitor of a particular step of ubiquitin-conjugation. Moreover, with minor changes, this protocol can be used to isolate E1:Ub or E2:Ub conjugates (e.g. activated ubiquitin conjugates) for use in the reconstituted protein mixture.

Identification of enzymes involved in the ubiquitin pathway from different sources have facilitated the cloning of corresponding genes. For instance, genes encoding E1 enzymes have been cloned from various organisms (see, for example, Adams et al. (1992) *Nature* 355:632–634; Handley et al. (1991) *Proc. Natl. Acad. Sci. USA* 88:258–262; Handley et al. (1991) *Proc. Natl. Acad. Sci. USA* 88:7456; Hatfield et al. (1990) *J. Biol. Chem.* 265:15813–15817; Kay et al. (1991) *Nature* 354:486–489; McCrath eg al. (1991) *EMBO J* 10:227–236; Mitchell et al. (1991)*Nature* 354:483–486; and Zacksenhaus et al. (1990) *EMBO J* 9:2923–2929). The sequences of various cloned E1 enzymes predict proteins of roughly 100 kd, and which contain the nucleotide-binding consensus sequence Gly-Xaa-Gly-Xaa-Xaa-Gly (McGrath et al. (1991) *EMBO J* 10:227–236).

In contrast to the ubiquitin-activating enzyme (E1), where it is generally believed that there are relatively few different species of the enzyme in a given cell, eukaryotic cells can express a large and diverse array of E2 enzymes. This remarkable variety of E2 enzymes, along with experimental evidence, has implicated the E2 enzyme as the principle determinant of substrate selectivity in the ubiquitin system. The E2 enzyme, as set out above, catalyzes isopeptide bond formation between ubiquitin and substrate proteins, either with or without the aid of a substrate recognition factor (ubiquitin-ligase protein; E3). So far, several major species of E2 enzymes have been identified and purifed by ubiquitin-affinity chromatography of extracts from rabbit reticulocytes (Pickart et al. (1985) *J Biol Chem* 260:1573–1581), yeast (Jentsch et al. (1987) *Nature* 329:131–134), and wheat (Sullivan et al. (1989)*Proc. Natl. Acad. Sci. USA* 86:9861–9865). Furthermore, many genes encoding E2 enzymes have been cloned and characterized with several human (and other mammalian) E2 enzymes having been cloned. For example, the cloning of human UBC5 (GenBank X78140) is described at Scheffner et al. (1994) *PNAS* 91:8797–8801; the cloning of human UBC2 (GenBank Z29328) is described at Kaiser et al. (1994); *J. Biol. Chem* 269:8797–8802; the cloning of human UBC1 is described at Kaiser et al. (1994) *FEBS Lett* 350:1–4; the cloning of other human ubiquitin conjugating enzymes, such as GenBank X53251 and M74525, are taught by Schneider et al. (1990) *Embo J.* 9:1431–1435 and Koken et al. (1991) *PNAS* 88:8865–8869, respectively. Still other human UBC's are described in the literature. (Koken et al. (1992) *Genomics* 12:447–453; Koken et al. (1991) *Proc. Natl. Acad. Sci. USA* 88:8865–8869; and Schneider et al. (1990) *EMBO J* 9:1431–1435.

The regulatory protein provided in the subject assay can be derived by purification from a cell in which it is exogenously expressed, or from a recombinant source of the protein. For example, cDNA clones are available for a number of regulatory proteins, including cyclin B (Pines et al. (1989) *Cell* 58:833–846); p53 (Oren et al. (1983) *EMBO J* 2:1633–1639); c-myc (Hann et al. (1988) *Cell* 52:185–195); N-myc (Curran et al. (1987) *Oncogene* 2:79–84); MATα2 (Hochstrasser et al. (1990) *Cell* 61:697–708); and E1A (Salvicek et al. (1988) *EMBO J* 7:3171–3180).

In each instance where a recombinant source of a protein is used in the subject assay, the manipulation of the gene encoding the protein and the subsequent expression of the protein can be carried out by standard molecular biological techniques. Ligating the polynucleotide sequence encoding the recombinant protein into a gene construct, such as an expression vector, and transforming or transfecting into host cells, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or obvious modifications thereof, can be employed to prepare and purify recombinant proteins of the ubiquitin-conjugating system by microbial means or tissue-culture technology for use in the subject assay.

The recombinant protein (e.g. E1, E2, CDC27, CDC16, the regulatory protein, etc.) can be produced by ligating the cloned gene, or a portion thereof, into a vector suitable for expression in either prokaryotic cells, eukaryotic cells, or both. Expression vehicles for production of recombinant proteins include plasmids and other vectors. For instance, suitable vectors for the expression of these proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see for example Broach et al. (1983) in *Experimental Manipulation of Gene Expression*, ed M. Inouye Academic Press, p. 83+). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pHβAPr-1-neo, EBO-pcD-XN, pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, as described below in Example 1, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In preferred embodiments, the expression vectors used to produce the recombinant proteins of the present invention are chosen to include at least one selectable marker for each cell line in which the vector is to be replicated or expressed. For instance, the vectors can be derived with sequences conferring resistance to ampicillin, chloramphenicol or kanomycin to facilitate amplification in *E. coli*. For selection in mammalian cells, such markers as the mammalian expressible *E. coli* ecogpt gene—which codes for a xanthine-guanine phosphoribosyl transferase (XGPRT) and allows selection of transfected HPRT⁻ mammalian cells with mycophenolic acid—can be utilized.

Furthermore, the recombinant protein can be encoded by a fusion gene created to have additional sequences coding for a polypeptide portion of a fusion protein which would facilitate its purification. For instance, Example 1 describes a fusion gene coding for a purification leader sequence comprising a poly-(His)/enterokinase cleavage site sequence at the N-terminus of the desired portion the protein, thereby enabling purification of the expressed fusion protein by affinity chromatography using a $Ni^{2+}$ metal resin. The purification leader sequence can then be subsequently removed by treatment with enterokinase (e.g., see Hochuli et al. 1987 *J. Chromatography* 411:177; and Janknecht et al. *Proc. Natl. Acad. Sci. USA* 88:8972).

Exemplification

The invention now being generally described, it will be more readily understood by reference to the following examples which are included merely for purposes of illustration of certain aspects and embodiments of the present invention, and are not intended to limit the invention.

EXAMPLE 1

Ubiquitin can be obtained from commercial sources, and the remaining protein components of the reconstituted protein system cloned from, for example, HeLa cells (ATCC CCL2). Briefly, polyadenylated RNA is isolated from cultured HeLa cells and first strand cDNA is prepared following standard protocols (c.f., Chomczynski U.S. Pat. No. 4,843, 155; and Sambrook et al. *Molecular Cloning: A Laboratory Manual*, CSHL Press, Cold Spring Harbor, N.Y. (1989)). PCR primers, designed to amplify DNA sequences encoding each of the component proteins, as well as provide convenient restriction sites to the PCR products, are used to isolate coding sequences for a human E1, human cyclin B, CDC27, CDC16, and UBC4, which are subsequently liguated into a pBluescript II KS+ phagemid (pKS+ Stratagene catalog no. 212207) for further manipulation. As described below, each of the component proteins genes are subsequently subcloned from pKS+ into other expression vectors to generate gene constructs for producing the recombinant proteins in either bacterial or insect cells. In some instances, the recombinant proteins can be provided with exogenous sequences to produce fusion proteins, where the additional sequences of the fusion protein facilitate its purification.

i) Human E1

Utilizing the primers 5'-(GC)$_3$AAGCTTATGTCCAGCTCGCCGCTGTCCAAG-3'(SEQ ID No. 5) and 5'-(GC)$_3$GGATCCTCAGCGGATGGTGTATCGGACATA-3'(SEQ ID No. 7), the coding sequence for a human E1 (SEQ ID No. 3) is amplified from a HeLa cell cDNA library. The PCR amplification product containing the E1 coding sequences is purified and cut with HindIII and BamHI (restriction sites provided by the PCR primers), and ligated into the pKS+ phagemid. The resulting pKS-E1 construct is amplified in XL 1-Blue Cells (Strategen catalog no. 260268), and double stranded construct purified.

A Hind III/fill to BamHI fragments containing the E1 coding sequence is isolated from the pKS-E1 construct, where "Hind III/fill" indicates that a Hind III overhand generated in the fragment is filled to form a blunt-end using Klenow and dNTPs. The E1 gene fragment is purified by agarose gel separation, and ligated into the baculorvirus vector pVL1393 (Invitrogen catalog no. V1392-20) previously cut with SmaI and BglII. The pVL1393-E1 construct is used to transfect spodoptera frugiperda (Sf9) cells (ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin* No. 1555, College Station, Tex.; Luckow et al. (1988) Bio/technology 6:47–55; and Miller et al., in *Genetic Engineering*, Vol. 8 (Setlow and Hollaender, eds) pp. 277–298, Plenum, N.Y.). Transfected cells are grown until the cells begin to lose their adherence to the culture plate surface, at which time the cells are harvested, collected by centrifugation, and lysed. The lysate is clarified by centrifugation to remove the cell wall debris, and the E1 containing lysate is applied to a sepharose-ubiquitin column (Hershko et al. (1983) *J. Biol. Chem.* 257:2537–2542) in the presence of ATP (e.g. 5 m MATP, 10 mM MgCl$_2$, and 0.2 mM clithiothreitol, 50 mM Tris-HCl (pH 7.2)). The column is washed several times with this buffer, and the E1 protein eluted with the following solutions: 1M KCl containing 50 mM Tris-HCl, pH7.2 (KCl eluate); the above Tris buffer, to remove salt; and finally 2 mM ATP and 0.04 mM sodium pyrophosphate in the above Tri buffer. The E1-containing eluate can be concentrated, as well as placed in new buffer solution, by centrifuge ultrafiltration with CentriPrep or Centricon membranes (Areicon Corp., MA.). Alternatively, the ubiquitin-immoblized E1 can be used, as described below, in the purification of E2 enzymes.

ii) Human UBC4

The UBC4 ubiquitin-conjugating enzyme (SEQ ID No: 4) is amplified and cloned from a HeLa cell cDNA library using the PCR primer sets 5'-(GC)$_3$AAGCTTTAYGARGGWGGWGT-YTTYTT-3' (SEQ ID No. 7), 5'-(GC)$_3$GAATTCACNGCRTAYTTYTTNGTCCCAYTC-3' (SEQ ID No. 8), and 5'-(GC)$_3$AAGCTTCCNGTNGGNGAYTTRTTYCAYTGGCA-3' (SEQ ID No. 9), 5'-(GC)$_3$GAATTCATNGTNARNGC-NGGCGACCA-3' (SEQ ID No. 10), and cloned into pBluescript II pKS+ as a Hind III-EcoRI fragment. After further amplification, the pKSUBC4 construct is cut with XhoI and EcoRI, and the fragment containing the UBC4 coding sequence sub-cloned into a pGEX vector (Pharmacia catalog no. PGEX-4T-2) previously digested with SalI and EcoRI. The resulting pGEX-UBC4 construct encodes a glutathione-S-transferase (GST)/E2 fusion, and is introduced into *E. coli* by transfromation, wit the transformants grown in liquid media (LB) in the presence of IPTG. Purification of GST/E2 fusion protein is by standard protocols (*Current Protocols in Molecular Biology*, eds. Ausubel et al. (NY:John Wiley & Sons, 1991); Pharmacia instruction booklet (for catalog no. 27-4570)) using a glutathione-sepharose column (Pharmacia catalog no. 27-4570). Treatment with thrombin removes the GST domain from the fusion protein.

Alternatively, the UBC4 coding sequence can be excised from the pkS-UBC4 construct as a HindIII-EcoRI fragment and ligated into pVL1393 cut with Sma I and Eco I. The E2 protein is produced in Sf9 cells, as described above, and purified on a sepharose-uibiquitin:E1 column. As above, a clarified lysate of the E2-producing insect cells, adjusted to 50 mM Tris-HCl (pH 7.2), 5 mM ATP, 10 mM MgCl$_2$, and 0.2 mM dithiothreitol, is applied to the ub:E1 column, washed, then eluted to remove any remaining ub:E1 (e.g. E2 will be exchanged for E1 on the column). UBC4 is then eluted from the column by washing with Tris buffer containing dithiothreitol.

iii) Human cyclin B1

Following similar protocols as described above, the human cyclin B1 gene can be cloned into the appropriate expression vector for recombinant production of the protein (see, for example, Pines et al. (1989) *Cell* 58:833–846). For instance, utilizing the primers 5'-(GC)$_3$GGATCCATGGCGCTCCGAGTC (SEQ ID No. 11) and 5'(GC)$_3$CTTAAGCTACGTACGGTGTC (SEQ ID No. 12), the human cyclin B1 coding sequence can be amplified by PCR, cut with BamHI and EcoRI, and ligated into pGEX-4T-2 (Pharmacia) to produce a GST-cyclin B fusion protein that can be purified according to the manufacturer's protocols.

iv) Human CDC27

The human CDC27 gene (SEQ ID NO: 2) can be manipulated, as above, to provide various recombinant forms of the protein, with expression in both prokaryotic and eukaryotic systems. For instance, the coding sequence of human CDC27 can be amplified from a human cDNA library with the PCR primers 5'-(GC)$_3$GGATCCATGACGGTGCTG (SEQ ID No. 13) and 5'-(GC)$_3$ TTCGAAAAATTCATCACT (SEQ ID No. 14), the amplified product cut with BamHI and HindIII, and that fragment cloned into the pRSET vector (Invitrogen). The pRSET-CDC27 construct is used to transfect JM109 *E. coli*, the resulting cultures lysed, and the poly (His)-tagged CDC27 purified on a ProBond (Invitrogen) Ni$^{2+}$-sepharose column according to the manufacturer's directions. The poly (His) sequence can be removed by treatment with enterokinase.

v) Human CDC16

A recombinant form of the human CDC16 protein can be generated by first cloning the CDC16 eDNA from the expressed sequence tag clone of ATCC deposit 85882 (see GenBank accessions T09436 and U18291). The coding sequence for the human CDC16 can be provided in any of a number of expression vectors to produce the recombinant protein as desired.

Alternatively, CDC27, such as the poly(His)-CDC27 described above, can be used to isolate CDC16 and other components of the MDC from cell lysates by affinity chromatography.

vi) Ubiquitin

Ubiquitin is available from commercial sources (Bovine ubiquitin, Sigma catalog no. 6253; yeast ubiquitin, Sigma catalog no. 2129). Various modified forms of ubiquitin are also available as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS (N-hydroxy-succinimide ester) using well-known techniques (biotinylation kit; Pierce catalog no. 214206, 203188 (6 atom spacer), or 2031114 (14 atom spacer)).

vii) Additional Reagents

For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtrite plates (Pierce catalog no. 15124); Maleic anhydride-activated polystyrene 96 well plates (Pierce catalog no. 15110); and antibody to human cyclin B (PharMingen catalog).

EXAMPLE 2

To generate the ubiquitin-conjugating system comprising a reconstituted protein mixture, portions of each of the preparations of purified components (described above), along with ubiquitin, are mixed together in a conjugation buffer comprising 50 mM Tris-HCl (pH7.4), 5 mM MgCl$_2$, 2 mM ATP, 0.1 mM DTT, and 5 µM ubiquitin. In a typical reaction, E1, UBC4, the target protein (cyclin B), and the MDC complex (either purified as described in Example 6, or reconstituted as above), are added to the conjugation buffer at approximately 100 ng each in a final reaction volume of 20–50 µL. The reconstituted ubiquitin-conjugating system is incubated at 25° C. for varying lengths of time (e.g. 0.5 to 30 minutes), in the presence of varying concentrations of a candidate agent (e.g. 0 to 50 mM), and the reaction quenched with iodoacetate and/or arsenite. Where either preconjugated E1:Ub or UBC4:Ub is used to genereate the mixture, the level of the conjugate in the reaction system can be increased to 5–10 µM, and free ubiquitin left out of the conjugation buffer. The levels of cyclin:Ub conjugates in the presence and absence of a candidate agent can be determined as described herein, taking into account statistical significance (e.g. the error of the particular assay employed) and appropriate controls.

EXAMPLE 3

$^{35}$S-labeled cyclin B, prepared by cell culture technique utilizing $^{35}$S-methionine, is incubated with combined purified components of a ubiquitin conjugating system as described in Example 2, including biotinylated ubiquitin. The reaction is conducted in a 96 well microtitre plate and stopped with iodoacetate. The reaction mixture is transferred to the wells of a streptavidin-coated microtitre plate and incubated to capture the complex of biotinylated ubiquitin and cyclin B (free biotinylated ubiquitin will also compete for binding sites on the well). The wells are washed with buffer (e.g. phosphate-buffered saline, or conjugation buffer lacking ubiquitin and ATP) to remove uncomplexed cyclin. Ubiquinated cyclin is detected by addition of scintillant to the well and counting in a scintillation instrument. Inhibition of the ubiquitin conjugation system by an added candidate agent is indicated by a reduced radioactive count

EXAMPLE 4

Cyclin B1 is incubated with combined purified components of a ubiquitin conjugating system as desribed above, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and cyclin (free biotinylatod ubiquitin will also compete for binding sites on the well). The wells are washed with buffer to remove uncomplexed cyclin. Next, the ub:cyclin complexes capatured on the plate are decorated with an antibody to cyclin B1. The wells are washed and binding of monoclonal antibody is detected by addition of peroxidase-conjugated antibody to mouse IgG (H+L) (Pierce catalog nos. 91430G and 91450G) and contacting with an appropriate substrate system, such as o-phenylenediamine dihydrochloride (Sigma catalog no. P9187).

EXAMPLE 5

A glutathione S-transferase (GST)-cyclin B fusion product is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and GST-cyclin (free biotinylated ubiquitin will also compete for binding silos on the well). The wells are washed with buffer to remove uncomplexed GST-cyclin. Binding of ubiquitinatod GST-cyclin is monitored with a detection system, based either on a biochemical assay for GST (e.g., 1- chloro-2,4-dinitrobenzene, Pharmacia catalog no. 27-4590-01) or an immunological assay using goat anti-GST antibody (Pharmacia catalog no. 27-4590-01).

EXAMPLE 6

Antibodies and Proteins

Purified monoclonal MPM-2 antibodies (Davis et al., 1983) were prepared by standard techniques. Rabbit antibodies were raised-against human UBC4 according to known methods. In immunoblotting experiments antisera used at a dilution of 1:300 recognized a major band of 15 kDa in crude Xenopus egg extract and in fraction Q1 that was absent from fraction Q2. The antibodies did not immunoprecipitate native UBC4. Monoclonal antibody 1C5 specific for E1 (Schwartz et al. (1992) *Proc. Natl. Acad. Sci. USA* 89:5542) was prepared according to standard methods. Rabbit antibodies raised against human CDC27 and CDC16 proteins were used for immunoblotting at a dilution of 1:2000. Immunoblots were visualized using the ECL detection system (Amersham).

Bovine ubiquitin was from Sigma. An N-terminal fragment of sea urchin cyclin B, consisting of residues 13–110, and a corresponding fragment containing a mutated destruction box (R42A, A44R) were expressed in *E. coli*, and purified as described (Holloway et al. (1993) *Cell* 73:1393). Recombinant human UBC4 and E1 were purified according to standard techniques.

Preparation of Extracts and High-Speed Supernatants

Different types of concentrated extracts were prepared from laid *Xenopus laevis* eggs. Interphase extracts were prepared as described (Murray (1991) *Methods Cell Biol.* 36:581), except that eggs were activated with the calcium ionophore A23187 (Calbiochem) at a concentration of 1 µg/ml. Cycloheximide was added to arrest the extracts in interphase. To generate mitotic Δ90 extracts, a bacterially-expressed, non-degradable 90 fragment of sea urchin cyclin B was added to interphase extracts at a concentration of 60 µg/ml. This keeps the cyclin degradation system constitutively activated (Glotzer et al. (1991) op. cit.). A different mitotic extract was prepared from non-activated metaphase II arrested eggs according to the protocol described by Kuang and colleagues for "mature oocyte extracts" (Kuang et al. (1991) *Proc. Natl. Acad. Sci. USA* 88:11530). Okadaic acid (Calbiochem) was added to a concentration of 1 µM which is known to activate the cyclin degradation system in such extracts (Lorca et al. (1991) *Mol. Cell. Biol.* 11:1171).

For the generation of high-speed supernatants, extracts were diluted 10-fold in buffer Q-A (20 mM Tris-HCl, pH 7.7, 100 mM KCl, 0.1 mM $CaCl_2$, 1 mM $MgCl_2$, 1 mM dithiothreitol (DTT) containing an energy-regenerating system (7.5 mM creatine phosphate, 1 mM adenosine triphosphate (ATP), 0.1 mM EGTA, 1 mM $MgCl_2$, pH 7.7) and okadaic acid (1 µM, mitotic extracts only), and were centrifuged for 1 h at 115,000×g at 4° C. The supernatant was reconcentrated to 50% of the original extract volume in Centriprep-10 concentrators (Amicon). Pellet and membrane fractions were separately resuspended in the dilution buffer, centrifuged again, and resuspended in 50% of the original volume. Extracts, pellet, membrane and supernatant fractions were stored at −70° C.

In some cases, the extracts from metaphase II eggs were thiophosphorylated to generate stably phosphorylated proteins, using the protocol described by Kuang et al. (1991; op. cit.) with modifications (data not shown). Briefly, protein from 500 ml of extract was precipitated with 0–40% ammonium sulfate, redissolved in 25 ml of extraction buffer (EB; 80 mM glycerophosphate, 15 mM $MgCl_2$, 20 mM EDTA, 3 mM DTT, pH 7.4) containing 1 µM okadaic acid and 1 mM ATP-γ-S (Boehringer) and clarified by centrifugation for 15 min in a SS34 rotor (Sorvall) at 15,000 rpm. The supernatant was applied to a 175 ml G25 column (Pharmacia) pre-equilibrated with EB containing okadaic acid and ATP-γ-S. The column was eluted with 100 ml of EB. Fractions containing protein or ATP-γ-S were pooled and incubated for 16 h at 4° C. and for an additional 2 h at room temperature. The resulting thiophosphorylated fraction was applied to a 50 ml Q Sepharose fast-flow column (Pharmacia). Bound proteins were eluted in two steps with EB containing 200 mM NaCl (QE-I) and with EB containing 400 mM NaCl (QE-II), respectively. Fractions were pooled into flow through, QE-I and QE-I, proteins were precipitated with 40% ammonium sulfate and the resulting pellets were stored at −70° C.

All fractionation was carried out at 4° C. Unless otherwise specified, interphase extracts and the corresponding mitotic Δ90 extracts were used as the starting material for all experiments. For generation of fractions Q1 and Q2, 20–40 ml of diluted S100 was applied to a 6 ml Resource Q column on an FPLC system (Pharmacia) equilibrated with buffer Q-A. Flow-through fractions were combined (Q1), the column washed with 5 column volumes, and bound proteins eluted with 0.5M KCl in Q-A. Eluted fractions were combined (Q2), desalted on PD10 columns (Pharmacia), a nd Q1 and Q2 reconcentrated to 50% of the original extract volume.

To generate fractions Q1A and Q1B, Fraction Q1 derived from 50 ml of diluted S100 was precipitated with 80% ammonium sulfate, redissolved in buffer S-A (10 mM PIPES-KOH, pH 6.5, 30 mM KCl, 1 mM DTT) and gel filtered into the same buffer. The fraction was applied to a 6 ml Resource S column on an FPLC system equilibrated with buffer S-A. After collection of the flow-through fraction (Q1A), the column was washed with 2 column volumes of buffer S-A, and bound proteins eluted with 0.5M KCl in S-A (Q1B). Q1A and Q1B were gel filtered into buffer Q-A and reconcentrated as described for fractions Q1 and Q2. Because fraction Q1B prepared this way contained a small amount of the 30 kDa activity, we raised the KCl concentration in buffer S-A during the Resource S chromatography step to 50 mM, and simplified the purification procedure by applying S100 directly to the Resource S column. This protocol generated a Q1B fraction that was not contaminated with the activity found in Q1A.

For analysis of Q1A and Q1B by gel filtration, 1–2 ml samples of concentrated Q1A or Q1B were separated on a Superdex 75 column (1.6×60 cm) equilibrated with buffer Q-A on an FPLC system (Pharmacia) at a flow rate of 0.75 ml/min. 5 ml fractions were collected and concentrated 10- to 25-fold. In some cases, ubiquitin or bovine serum albumin (BSA) was added to the fractions to a final concentration of 0.2 mg/ml before reconcentration.

For further fractionation of proteins in Q2, 40 ml of mitotic S100 was applied to the 6 ml Resource Q column. Bound proteins were eluted with six column volumes of a linear salt gradient (0–500 mM KCl in buffer Q-A). 2.5 ml fractions were collected, desalted on PD10 columns and reconcentrated to 0.5 ml. Similar amounts of S100 fractions prepared from metaphase II extracts were fractionated using the same protocol. Thiophosphorylated QE2 fractions (100 mg protein) were also separated this way.

For the determination of sedimentation coefficients, 0.5 ml of a fraction containing MDC obtained by separation of QE-II on Resource Q was further analyzed by sucrose gradient centrifugation. 15–40% sucrose gradients were centrifuged for 13.5 h at 37,500 rpm in a SW40 rotor (Beckman). 0.85 ml fractions were collected using an Isco gradient fractionator, diluted 1:4 with buffer Q-A and concentrated to approximately 150 µl each. The positions of the 15S p97-ATPase (Peters et al. (1990) *EMBO J.* 9:1757) and of a 10S complex of elongation factors (Belle et al. (1989) *FEBS Lett.* 255:101); and data not shown) separated in the same sucrose gradient were used to estimate the S-value of MDC.

For the determination of the apparent molecular weight of MDC, 0.2 ml of a reconcentrated Q column fraction was applied to a 24 ml Superose 6 column (Pharmacia). Fractions of 1 ml were collected at a flow rate of 0.5 ml/min and reconcentrated to 0.1 ml and assayed against interphase S100. The apparent molecular weight was estimated by comparison to the elution profile of a standard mixture of thyroglobulin, ferritin, and bovine serum albumin (Pharmacia).

N-terminal fragments of sea urchin cyclin B (residues 13–110) containing either a wild type or mutated (R42A, A44R) destruction box were labeled to a specific activity of ~100 µCi/µg protein using the chloramine T procedure (Parker, (1990) *Methods. Enzymol.* 182:721). Ubiquitination assays were performed in a total volume of 5 or 10 µl and contained energy-regenerating system, 1.25 mg/ml ubiquitin and 12.5 ng (100 mM) labeled substrate. Reactions were incubated at room temperature for 10–15 min and quenched by addition of sodium-dodicyl-sulfate dodecyl-sulfate (SDS)-sample buffer, and analyzed by SDS-polyacrylamide gel electrophoresis (SDS-PAGE). Dried gels were then analyzed by autoradiography or by phosphor imaging using a Molecular Dynamics phosphorimager.

For assay of column fractions against interphase S100, reactions contained 3 µl of column fraction, 1.25 µl of interphase S100, ubiquitin, and energy-regenerating system in a total volume of 5 µl. For assay against E1 and UBC4, reactions contained 3 µl column fraction, 130 µg/ml recombinant human E1, 25 µl/ml recombinant human UBC4, ubiquitin and energy-regenerating system in a final volume of 5 µl.

For E1-ubiquitin thioester assays, column fractions were incubated with 0.3 µg iodinated ubiquitin (10 µCi/µg) in a total volume of 10 µl in the presence of 5 mM Tris-HCl (pH 7.7), 10 mM $MgCl_2$, 1 mM ATP, 0.1 mM DTT, and 1 U inorganic pyrophosphatase (Sigma). After 5 min at room temperature, reactions were stopped by addition of 10 µl urea sample buffer (120 mM Tris-HCl, pH 6.8, 4% SDS, 4M urea, 20% glycerol), and reaction products analyzed by non-reducing SDS-PAGE and autoradiography. For the detection of E2-ubiquitin thioesters, assays were performed as described, except that reaction mixtures contained either 1 µg recombinant wheat E1 (Hatfield et al. (1990) *J. Biol. Chem.* 265:16376), partially purified Xenopus E1, or purified recombinant human E1.

MPM-2 monoclonal antibody was purified from mouse hybridoma ascites as described (Kuang et al. (1989) *Proc. Natl. Acad. Sci. USA* 86:4982). 0.25 volumes of purified MPM-2 antibody (10 mg/ml) or control antibody (purified total mouse IgG (Sigma), 10 mg/ml) was added to fraction Q1 or Q2 (final volume 13.5 µl) and the mixture incubated for 20 minutes on ice. Protein A-Sepharose beads (5 82 1; Sigma) were then added, and the incubation continued on ice for 40 minutes with frequent mixing. Beads were removed by centrifugation, and the supernatant tested for ubiquitination activity.

For CDC27 immunodepletion and reconstitution experiments, one volume of crude anti-CDC27 rabbit serum or preimmune serum was incubated with two volumes of protein A-sepharose beads (Biorad) for 2 hours at 4° C. Beads were washed 5 times in buffer Q-A, and then incubated in five volumes of the appropriate fraction for 2 hours at 4° C. Beads were washed 5 times in Q-A buffer containing 500 mM KCl, and three times in buffer Q-A. For immunoblot analysis, 10 µl of washed beads were eluted with 100 µl SDS-sample buffer and boiled; 20 µl was analyzed by SDS-PAGE and subsequent immunoblotting. For ubiquitination assays, 5 µl of washed beads was incubated with 6 µl of a mix containing either interphase S100, or with a mixture of recombinant E1 (260 µg/ml) and UBC4 (50 µg/ml); both mixes contained energy-regenerating system, ubiquitin, and labeled substrate at the concentrations indicated above.

As a substrate for the ubiquitin conjugation reaction, we used an iodinated N-terminal fragment of sea urchin cyclin B, consisting of residues 13–110. We monitored the formation of radiolabeled cyclin-ubiquitin conjugates by SDS-PAGE and autoradiography. The ubiquitination and degradation of this protein is dependent upon the cell-cycle state of crude extracts and requires an intact destruction box (Holloway et al. (1993) *Cell* 73:1393; and data not shown). As a source of factors required for cyclin ubiquitination, we prepared concentrated interphase extracts from Xenopus eggs activated with calcium ionophore in the presence of cycloheximide. Stable mitotic extracts that constitutively degrade cyclin B were then obtained by addition of the non-degradable Δ90 fragment of sea urchin cyclin B (Glotzer et al. (1991) op cit.).

Our protocol for the separation of mitotic Xenopus extracts into fractions required for cyclin ubiquitination activity is shown in FIG. 1. As a first step, we prepared pellet, membrane, and supernatant (S100) fractions by high-speed centrifugation of diluted, crude mitotic extracts. Okadaic acid was added to prevent reversal of the mitotic state. Cyclin ubiquitination activity was recovered in the S100 fraction after reconcentration to the original volume, as indicated by the ladder-like appearance of higher-molecular-weight species upon SDS-PAGE analysis. Ubiquitin conjugates were observed within one to two minutes of incubation in the mitotic supernatant, and reached a steady state within five minutes (data not shown). The substrate was also degraded in this fraction with a half-life of approximately five minutes, similar to that observed in crude extracts (data not shown). No ubiquitination activity was detectable in the washed pellet or membrane fractions by SDS-PAGE analysis.

We fractionated mitotic S100 by anion exchange chromatography, using Resource Q as a resin, yielding a flow through fraction (Q1) and a 0.6M KCl eluate (Q2). While neither fraction alone catalyzed cyclin ubiquitination, mixing the fractions fully reconstituted activity (FIG. 1C). A destruction box mutant (R42A, A44R) produced only low-molecular-weight conjugates. To determine whether both of these fractions were mitotically regulated, we prepared Q1 and Q2 from interphase S100 (designated $Q1^i$ and $Q2^i$). Cyclin ubiquitination was observed when Q1 was replaced by $Q1^i$ but not when Q2 was replaced by $Q2^i$, indicating that only Q2 is mitotically regulated.

We had observed that addition of the monoclonal antibody MPM-2, which recognizes a subset of proteins phosphorylated in mitosis, could inhibit cyclin ubiquitination and degradation when added to crude mitotic extracts (data not shown). We found that immunodepletion of fraction Q2 with the MPM-2 antibody strongly inhibited cyclin ubiquitination, while depletion of fraction Q1 had no effect. Control depletions using total mouse IgG or an unrelated monoclonal antibody were not inhibitory. This result further suggests that Q2 is subject to mitotic regulation.

To identify components in the unregulated fraction required for cyclin ubiquitination, we further fractionated Q1 by gel filtration and tested each fraction for its ability to complement Q2. We found complementing activity in a broad molecular weight range corresponding to 15–40 kDa, suggesting that multiple components in Q1 might each be sufficient to complement Q2 (data not shown). To test this idea, we fractionated Q1 by Resource S chromatography, and generated a flow-through fraction (Q1A) and a 0.6M KCl eluate (Q1B). Each fraction was sufficient to complement Q2, and was therefore further fractionated by gel filtration. The peak of activity in fraction Q1A eluted at 70 ml, corresponding to a molecular weight of ~30 kDa; activity in fraction Q1B peaked at 81 ml, corresponding to ~20 kDa. The pattern of ubiquitin conjugates generated by Q1A and Q1B was somewhat different: Q1A favored the production of low-molecular-weight conjugates, whereas Q1B generated higher-molecular-weight conjugates, suggesting that these activities are distinct. Ubiquitination mediated by both Q1A and Q1B required an intact cyclin destruction box (data not shown).

Figure 2:
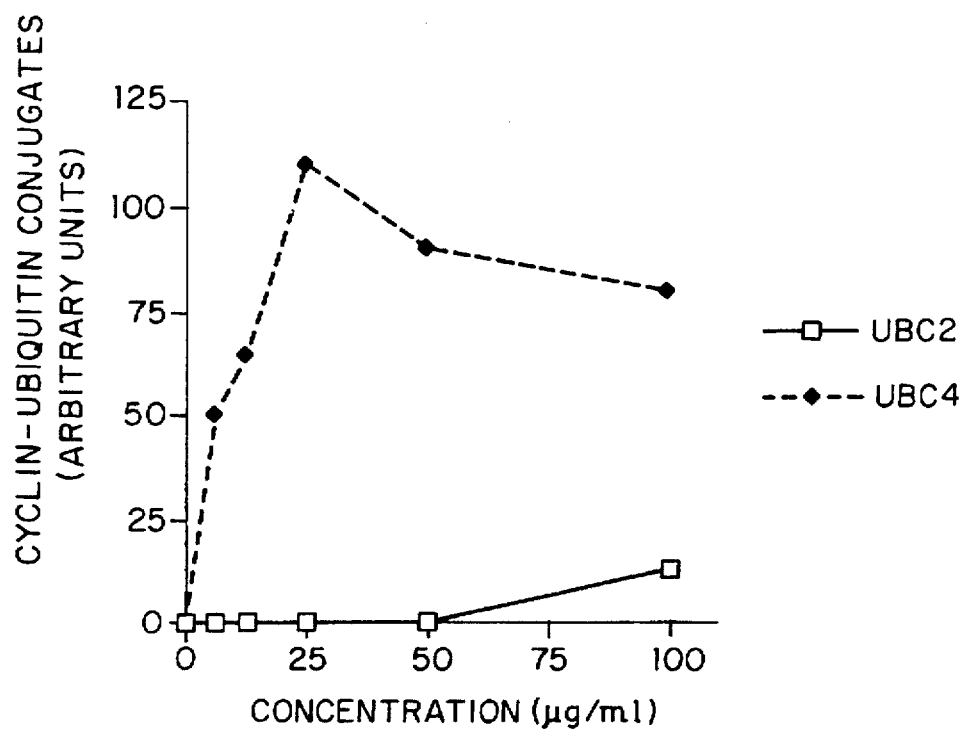
FIG. 2 shows the dose-response curve of the ability of UBC2 and UBC4 to complement fraction Q2.

As ubiquitin-conjugating enzymes typically range in size from 14 to 28 kDa, we tested gel filtration fractions derived from Q1A and Q1B for the presence of E2s by determining whether specific thioesters were formed in the presence of radiolabeled ubiquitin and purified E1. Fraction Q1A contained multiple ubiquitin thioesters of 24–34 kDa that copurified with cyclin-conjugating activity. By contrast, the activity in fraction Q1B copurified with a single predominant thioester of 22 kDa, suggesting the presence of a 15–16 kDa E2. As this thioester did not cofractionate with the peak of activity in fraction Q1A, there appear to be at least two different E2s in fraction Q1 sufficient to complement Q2. Only very few E2s characterized to date would be expected to behave chromatographically like the activity in fraction Q1B to bind cation exchange resins. One of these, a Xenopus homolog of UBC9, did not cofractionate with activity (data not shown). Another is represented by the UBC4/5 class of proteins, homologs of which have been demonstrated to bind cation exchange resins (Girod and Vierstra (1993) *J. Biol. Chem.* 268:955; Scheffner et al. (1993) *Cell* 75:495). Fraction Q1B showed strong UBC4 immunoreactivity that cofractionated with cyclin ubiquitination activity during gel filtration, while fraction Q1A contained only a small amount of UBC4 that did not copurify with the majority of activity. Therefore, we tested whether bacterially-expressed and purified human UBC4 was sufficient to complement fraction Q2. UBC4 supported cyclin ubiquitination in a dose-dependent fashion (FIG. 2). Strong complementation was observed at 6 µg/ml, the lowest concentration tested, and became maximal at 25 µg/ml. Quantitative immunoblotting demonstrated that UBC4 is present in fraction Q1 at a concentration of approximately 4 µg/ml (data not shown). In contrast, other purified E2s such as human CDC34 had no effect, even at high dose; human UBC2 only weakly supported cyclin ubiquitination (FIG. 2). This difference was not due to a difference in ability to accept ubiquitin from E1, because UBC2, UBC4 and CDC34 formed similar amounts of ubiquitin thioesters (data not shown). A destruction box mutant yielded only low molecular weight conjugates in the presence of recombinant UBC4, suggesting that substrate specificity is maintained in this reconstituted system.

Immunoblotting demonstrated the presence of E1 in fraction Q2 only (data not shown); its activity did not appear cell-cycle regulated as both Q2 and Q2$^i$ supported formation of a prominent ~120 kDa E1-ubiquitin thioester. Neither purified Xenopus E1 nor recombinant E1 was able to complement fraction Q2, suggesting that Q2 contained additional components required for cyclin ubiquitination. To identify mitotically-regulated components, mitotic S100 was applied to the Resource Q column and eluted with a linear 100–600 mM KCl gradient. Fractions were gel filtered, reconcentrated, and tested for their ability to complement interphase S100, which should contain all of the non-mitotically-regulated components. Interphase S100-complementing activity eluted as a major peak at 400 mM KCl (Fraction 11). E1, as measured by thioester formation with radiolabeled ubiquitin, eluted at approximately 200 mM KCl (Fractions 4 and 5). As expected, the E1-containing fractions did not strongly complement interphase S100. The peak fraction retained destruction-box dependence when assayed against interphase S100. Significantly, the peak fraction was sufficient to complement a mixture of recombinant E1, UBC4 and ubiquitin, suggesting that this activity did not simply convert the inactive interphase fraction into an active mitotic fraction. Identical results were obtained using mitotic S100 prepared from three different sources: cyclin Δ90-activated extracts, extracts from metaphase-II-arrested eggs, or egg extracts that had been thiophosphorylated to stabilize mitotic phosphorylation as described above (data not shown). These data suggest that the mitotically-regulated activity contains a mitosis-specific cyclin-ubiquitin ligase, as it can complement either interphase S100 or a mixture of purified E1 and UBC4.

To further characterize the mitotic activity in fraction Q2, we generated a Q eluate fraction from thiophosphorylated mitotic extracts that we refer to as fraction QE2 (see above). This fraction was reapplied to the Resource Q column, and the peak of activity, eluting at 400 mM KCl, was gel-filtered, reconcentrated, and fractionated by sucrose gradient centrifugation. A peak of interphase S100-complementing activity sedimented as a large discrete complex of approximately 20–22S. Peak fractions could also complement recombinant E1 and UBC4 (data not shown). Fractionation of the 400 mM Q eluate over a Superose 6 column indicated an apparent molecular weight between $1 \times 10^6$ and $1.5 \times 10^6$ Da (data not shown).

CDC16 and CDC23 have been demonstrated to physically interact with CDC27 in yeast (Lamb et al. (1994) *EMBO J.* 13:4321). In human cultured cells, CDC16 and CDC27 are components of an approximately 20S complex (data not shown). Therefore, we tested the peak sucrose gradient fractions described above for the presence of these proteins. Immunoblot analyses were performed using antibodies generated against human homologs of CDC16 and CDC27. It was found that CDC27 and CDC16 both cofractionated with activity. The corresponding preimmune sera showed no reactivity (data not shown). Further immunoblotting experiments revealed that both proteins also cofractionated with ubiquitination activity during Resource Q and gel filtration chromatography (data not shown). We found that CDC27 derived from QE2 migrated heterogeneously on SDS-PAGE analysis, with a relative molecular weight ($M_r$) of 115–140 kDa. CDC27 derived from interphase extracts migrated with an $M_r$ of approximately 100 kDa, suggesting that CDC27 is modified in mitosis (see below). CDC16 also appears to be modified in mitosis, as it migrated with an $M_r$ corresponding to 72 kDa in interphase extracts and 74 kDa in mitotic extracts.

To further examine the role of CDC27 and CDC16 in cyclin B ubiquitination, we immunodepleted fraction QE2 with antibodies raised against the human homolog of CDC27, and assayed the supernatant for ability to complement interphase S100. Immunodepletion of fraction QE2 completely inhibited its ability to complement interphase S100, while preimmune sera had no effect. This treatment effectively depleted the majority of CDC27 protein, and also removed a substantial portion of the CDC16 protein, suggesting that, as in yeast and humans, the two proteins form a complex (see below). Antisera raised against human CDC16 were not effective in immunodepleting either CDC16 or CDC27 proteins, nor did they deplete ubiquitin-conjugating activity (data not shown).

We next tested whether stringently-washed CDC27 immunoprecipitates derived from fraction QE2 were sufficient to complement interphase S100. CDC27 antibodies or preimmune antibodies were bound to protein A beads, washed, and incubated with fraction QE2 for 2 hours at 4° C. Beads were subsequently washed 5 times in buffer containing 500 mM KCl, and three times in buffer containing 100 mM KCl. CDC27 antibody beads derived from QE2 were capable of complementing interphase S100. This activity required the presence of an intact cyclin destruction box for generation of high-molecular weight conjugates.

We also tested the mitotic immunoprecipitate in a defined system composed of recombinant E1, UBC4, and purified ubiquitin. A CDC27 immunoprecipitate complemented these defined components, while the preimmune immunoprecipitate did not. The production of high molecular weight conjugates was reduced when the cyclin destruction box mutant was assayed. However, the discrimination between the wild-type and mutant substrate was not as strong when the CDC27 immunoprecipitate was tested against E1 and UBC4 as it was when tested against interphase S100. The reduced specificity in the defined reaction is unlikely to be related to the use of purified UBC4, because destruction-box dependence of the reaction is fully maintained when UBC4 is used to complement total fraction Q2 (as described supra). This may indicate that components required for full destruction-box-dependence may be partially lost during immunoprecipitation.

To determine whether CDC16 is present in a complex with CDC27, we immunoprecipitated CDC27 from either crude extracts or supernatant fractions. After stringent washing, we analyzed the immunoprecipitates for the presence of CDC27 and CDC16 by immunoblotting. We found that CDC27 was immunoprecipitated from crude interphase and mitotic extracts, and from interphase S100 and QE2 fractions. As described earlier, CDC27 derived from crude interphase extracts or S100 migrated with a relative molecular weight ($M_r$) of 100 kDa on denaturing polyacrylamide gels. However, when derived from a crude mitotic extract, slower migrating forms became apparent. This effect was enhanced by thiophosphorylation, because CDC27 derived from fraction QE2 had a further reduced mobility. Analysis of the immunoprecipitates by immunoblotting with CDC16 antibodies revealed that CDC16 co-immunoprecipitated with CDC27 under all of the conditions tested. The mobility of CDC16 also appeared to be reduced when derived from either crude mitotic extracts or fraction QE2, suggesting that it may also be modified in mitosis. These data suggest that at least a fraction of CDC16 is tightly associated with CDC27 in both interphase and mitosis.

The proteolysis of cyclin is a key event in the cell cycle that irreversibly signals exit from mitosis. Through the activation of cdc2 kinase, a process is initiated that targets cyclin for destruction by the ubiquitin system (Murray et al. (1989) *Nature* 339:280; Felix et al., (1990) *Nature* 346:379). Mitotic cyclins share a small conserved sequence, the destruction box, which is necessary for ubiquitination and subsequent proteolysis (Glotzer et al. (1991) op. cit.). To determine the basis of the substrate and cell cycle specificity of cyclin ubiquitination, we have fractionated mitotic extracts to identify components required for this process. In addition to the universally-required components, E1 and ubiquitin, we have found three distinct activities that can reconstitute mitotic cyclin ubiquitination. The first two activities are a set of ubiquitin conjugating enzymes that include UBC4, known to be involved in the conjugation of ubiquitin to many cellular proteins. The third is a novel 20S complex, which we term the Mitotic Destruction Complex (MDC), that contains homologs of two yeast proteins required for anaphase. This complex, which meets the functional criteria for a ubiquitin-protein ligase, is the major determinant of both substrate and cell cycle specificity in the cyclin ubiquitination system.

All ubiquitin conjugation reactions require the participation of at least one of a large family of ubiquitin conjugating enzymes. These enzymes have functional specificity that has been demonstrated both genetically and biochemically (see, e.g., Jentsch (1992) *Ann. Rev. Genet.* 26:179), but it is unclear how such specificity arises. Specific E2 requirements would be expected if E2s recognized and transferred ubiquitin to their substrates directly; however, few E2s appear to have this ability, and the physiological relevance of these reactions remains unclear. Alternatively, E2 functional specificity may arise as a consequence of interaction with a specific E3. This possibility seems especially likely in light of the recent finding that, at least in certain cases, E2s can transfer ubiquitin from E1 to E3 (Scheffner et al. (1995) *Nature* 373:81). In this model, both substrate recognition and ubiquitin conjugation would be catalyzed by the E3. Identification of the specific E2s involved in a particular ubiquination reaction may therefore reveal more about the nature of the E3 involved than about how substrates are recognized.

We find at least two unregulated ubiquitin conjugating enzymes in Xenopus extracts that can complement MDC and E1 to ubiquitinate cyclin B. Both of these E2 activities support a destruction-box-dependent reaction, suggesting that they act through a common recognition mechanism. In preliminary experiments, we have not seen any synergy between the two E2 activities. Until we can effectively immunodeplete these proteins from crude extracts and measure degradation, as well as ubiquitination, it will be difficult to assess their relative physiological importance.

Our data strongly suggest that one of the two E2 activities is a Xenopus homolog of UBC4. This protein copurifies with activity over ion exchange and gel filtration chromatography, and recombinant human UBC4 can fully complement destruction-box dependent cyclin ubiquitination at concentrations similar to those found in our fractions. The second E2 activity in our fractions remains unidentified. This E2 has a larger apparent molecular weight than UBC4 and may correspond to the recently-described activity in clam eggs called E-2C, for which structural information has not yet been reported (Hershko et al. (1994) *J. Biol. Chem.* 269:4940). The Xenopus homolog of UBC9, an enzyme implicated in cyclin degradation in yeast (Seufert et al. (1995) *Nature* 373:78), does not cofractionate with either of the two activities.

UBC4 has been implicated in the degradation of many different proteins. In yeast, it is required in conjunction with its close homolog UBC5 for the turnover of abnormal proteins (Seufert and Jentsch (1990) *EMBO J.* 9:543), and for the degradation of the transcription factor MATα2 (Chen et al. (1993) *Cell* 74:357). A UBC4 homolog found in wheat germ extract appears capable of supporting ubiquitin conjugation to many proteins in vitro (Girod and Vierstra (1993) *J. Biol. Chem.* 268:955). Mammalian homologs of UBC4 have been shown to participate in the ubiquitination of p53 catalyzed by the E6AP/E6 complex (Scheffner et al. (1994) *Proc. Natl. Acad. Sci. USA* 91:8797). These data suggest that the UBC4/5 family of E2s has the ability to interact with multiple E3s to ubiquitinate a large number of target proteins. The involvement of UBC4 in such varied ubiquitination reactions makes it an unlikely determinant of substrate specificity in the cyclin ubiquitination system.

Mutation of UBC4 family members (UBC4, 5) in yeast has not been reported to cause a clearly-defined cell cycle arrest (Seufert and Jentsch (1990) op. cit.). This could be due to either the pleiotropy of the mutation or to a redundancy in E2 function required for cyclin ubiquitination.

Without wishing to be bound by any particular theory, these data suggest that the cell cycle specificity of cyclin ubiquitation is mediated by the Mitotic Destruction Complex, which contains homologs of the yeast proteins CDC27 and CDC16, both of which are required for anaphase. When tested against the inactive S100 fraction from interphase cells, partially purified MDC will reconstitute cyclin ubiquitination to levels found in mitotic extracts. Reconstitution experiments with purified components indicate that MDC plays a direct role in the ubiquitination reaction, and does not simply serve as a regulator of ubiquitination in interphase extracts.

The CDC16 and CDC23 proteins form a complex with the CDC27 protein (Lamb et al. (1994), op. cit.). Each of these proteins contains several TPR motifs which may mediate protein interactions in this complex. These three genes are required for the onset of anaphase in yeast, and also in mammals, as injection of antibodies specific for human CDC27 result in metaphase arrest (data not shown). Using antibodies generated against the human homologs of CDC27 and CDC16, we have shown that they are present in MDC. CDC27 antibodies immunodeplete the mitotically-regulated ubiquitin-protein ligase activity from mitotic fractions, and immunopurified CDC27 complexes can reconstitute cyclin ubiquitination in a defined system composed of recombinant E1 and UBC4, purified ubiquitin, and ATP.

Formally MDC functions as a ubiquitin protein ligase as it is required for the transfer of ubiquitin from an E2, such as UBC4, to the substrate. Two distinct types of ligases have been cloned. Yeast UBR1 mediates N-end rule degradation (Varshavsky (1992) Cell 69:724); mammalian E6AP participates in p53 ubiquitination (Huibregtse et al. (1991) EMBO J. 10:4129; Huibregtse et al. (1993) Mol. Cell Biol. 13:775; Scheffner et al. (1993) Cell 75:495) and shares C-terminal homology with a family of other proteins (Scheffner et al., 1995 op. cit.), which may also function as E3s. UBR1 and E6AP do not share homology with each other or with CDC27, CDC16, or CDC23. Recently it has been demonstrated that E6AP can accept ubiquitin from UBC4, forming a thioester at a conserved cysteine residue essential for ligase activity (Scheffner et at., 1995 op. cit.). We have not yet been able to observe the formation of a similar thioester with MDC, but we have found that MDC activity is sensitive to the sulfhydryl-reactive reagent N-ethyl maleimide (data not shown).

The activation of cyclin B-cdc2 kinase is required for the activation of cyclin degradation (Murray et at., (1989) op. cit.; Luca et al. (1991) EMBO J. 10:4311)). Purified cdc2 kinase triggers cyclin degradation in interphase extracts (Felix et al., 1990), however there is a 15-minute lag period preceding activation, suggesting that the activation of MDC by cdc2 kinase may not be not direct. Furthermore, the MPM-2 monoclonal antibody, which recognizes a discrete set of mitotic phosphoproteins, can deplete MDC activity from crude fractions (see above), and can immunoprecipitate CDC27 and CDC16 (data not shown). Phosphorylation of this epitope appears to be mediated, at least in part, by kinases distinct from cdc2 (Kuang and Ashom (1993) J. Cell Biol. 123:859). Therefore, these kinases provide interesting candidates for regulators that function downstream of cdc2 kinase to contribute to the activation of MDC in mitosis. Interestingly, we observed a dramatic upward mobility shift for mitotic CDC27, as compared to the interphase form, and a small shift for CDC16. Preliminary experiments indicate that treatment of CDC27 immunoprecipitates with phosphatase can completely reverse this mobility shift (data not shown), suggesting that altered mobility is a consequence of mitotic phosphorylation. Such, large shifts have been seen for other MPM-2 epitopes, such as cdc25 (Kumagai and Dunphy (1992) Cell 70:139; Kuang et al. (1994) Mol. Biol. Cell 5:135). During the course of mitotic activation, the CDC27 upshift precedes the activation of cyclin ubiquitination, suggesting either a requirement for a threshold level of modification or the existence of additional controls.

Our immunoprecipitation results indicate that CDC27 and CDC16 are associated in both mitosis and interphase. It is therefore possible that an assembled but inactive form of MDC is present in interphase. We are currently characterizing the interphase form of MDC to determine how it becomes activated in mitosis.

Biochemical and genetic evidence have now converged to suggest that cyclin degradation and sister chromatin segregation are mediated by a common set of components including CDC16, CDC23, and CDC27. This complex may have functions in addition to cyclin ubiquitination, as certain mutant alleles of CDC16 and CDC27 block anaphase progression but do not interfere with cyclin degradation. One such function of this complex might be the ubiquitination of substrates other than mitotic cyclins whose degradation is required for the onset of anaphase. The existence of such proteins is suggested by the finding that an N-terminal fragment of cyclin B can inhibit the onset of anaphase in extracts that contain no other cyclin than exogenously added non-degradable cyclin (Holloway et al. (1993) op. cit.). Furthermore, methylated ubiquitin interferes with sister chromatin separation, suggesting the involvement of ubiquitin-mediated proteolysis in this process. MDC may therefore ubiquitinate several proteins whose degradation is required for anaphase, explaining why some but not all CDC16 alleles interfere with cyclin degradation in yeast. Alternatively, it is of course also possible that MDC has functions which are independent of its ubiquitin protein ligase activity.

Why the cyclin-ubiquitin ligase is contained in such a large complex is presently a mystery. Some insight into this problem may be found in the observation in fungi and mammalian cells that CDC27 and CDC16 localize to the mitotic spindle and centrosomes (Mirabito and Morris (1993) J. Cell Biol. 120:959), structures that have also been found to be associated with MPM-2 antigens and cyclin B (Engle et al. (1988) Cell Motil. Cytoskeleton 10:434; Bailly et al. (1992) J. Cell Sci. 101:529; Debec and Montmory (1992) Biol. Cell 75:121; Maldonado and Glover (1992) J. Cell Biol. 116:967; Vandre et al. (1986) Eur. J. Cell Biol. 41:72). The association of MDC with these structures may be important for its regulation, transmitting information regarding the state of spindle assembly to the mitotic degradation machinery. Additional levels of control may be imposed by activities such as cytostatic factor that arrest cell division at metaphase II of meiosis. MDC may therefore serve as a common target of controls that regulate the onset of anaphase.

All of the above-cited references and publications are hereby incorporated by reference.

Equivalents

Those skilled in the art will recognize, or be able to ascertain using no more than routine experimentation, numerous equivalents to the specific assay and reagents described herein. Such equivalents are considered to be within the scope of this invention and are covered by the following claims.

We claim:

1. An assay for identifying an inhibitor of ubiquitin-mediated proteolysis of a cell-cycle regulatory protein, comprising:
   (i) providing a cell-free ubiquitin-conjugating system, other than a whole lysate, which system comprises a cell-cycle regulatory protein, an E2 enzyme, a mitotic destruction complex (MDC), including CDC27 and CDC16 and ubiquitin, under conditions which promote MDC-dependent ubiquitination of the regulatory protein, wherein one or both of the CDC27 or CDC16 is provided to the system as a purified, semipurified or recombinant preparation; CDC27 and CDC16;
   (ii) contacting the ubiquitin-conjugating system with a candidate agent;
   (iii) measuring a level of ubiquitination of the regulatory protein in the presence of the candidate agent; and
   (iv) comparing the measured level of ubiquitination in the presence of the candidate agent with a level of ubiquitination of the regulatory protein in the absence of the candidate agent,
wherein a statistically significant decrease in ubiquitination of the regulatory protein in the presence of the candidate agent is indicative of an inhibitor of ubiquitination of the regulatory protein.

2. An assay for identifying an inhibitor of ubiquitin-mediated proteolysis of a cell-cycle regulatory protein, comprising:
   (i) providing a ubiquitin-conjugating system, which system comprises a reconstituted protein mixture including a cell-cycle regulatory protein, an E2 enzyme, a mitotic destruction complex (MDC) including CDC27 and CDC16, and ubiquitin, under conditions which promote MDC-dependent ubiginirination of the regulatory protein;
   (ii) contacting the ubiquitin-conjugating system with a candidate agent;
   (iii) measuring a level of ubiquitination of the regulatory protein in the presence of the candidate agent; and
   (iv) comparing the measured level of ubignitination in the presence of the candidate agent with a level of ubiquitination of the regulatory protein in the absence of the candidate agent,
wherein a decrease in ubiquitination of the regulatory protein in the presence of the candidate agent is indicative of an inhibitor of ubiquitination of the regulatory protein.

3. The assay of claim 2, wherein the cell-cycle regulatory protein is selected from the group consisting of a cyclin, p53, myc, and fos.

4. The assay of claim 2, wherein the MDC comprises a 20S complex isolated from a mitotically-regulated cell lysate fraction.

5. The assay of claim 2, wherein the ubiquitin is provided in a form selected from the group consisting of:
   (i) an unconjugated ubiquitin, in which case the ubiquitin-conjugating system further comprises an E1 ubiquitin-activating enzyme (E1), an E2 ubiquitin-conjugating enzyme (E2), and adenosine triphosphate;
   (ii) an activated E1:ubiquitin complex, in which case the ubiquitin-conjugating system further comprises an E2; and
   (iii) an activated E2:ubiquitin complex.

6. The assay of claim 2, wherein the E2 enzyme is selected from the group consisting of UBC4 and UBC5.

7. The assay of claim 2, wherein at least one of the ubiquitin and the regulatory protein comprises a detectable label, and the level of ubiquitin-conjugated regulatory protein is quantified by detecting the label in at least one of the regulatory protein, the ubiquitin, and the ubiquitin-conjugated regulatory protein.

8. The method of claim 7, wherein the label is selected from the group consisting of radioisotopes, fluorescent compounds, enzymes, and enzyme co-factors.

9. The assay of claim 7, wherein the detectable label is a protein having a measurable activity, and the regulatory protein is fusion protein including the detectable label.

10. The assay of claim 2, wherein the amount of ubiquitin-conjugated regulatory protein is quantified by an immunoassay.

11. An assay for identifying an inhibitor of ubiquitin-mediated proteolysis of a cyclin protein, comprising:
    (i) providing a ubiquitm-conjugating system, comprising a reconstituted protein mixture including
        a cyclin protein,
        an E2 enzyme,
        a mitotic destruction complex including a CDC27 protein and a CDC16 protein, and
        ubiquitin,
        under conditions which promote ubiquitination of the cyclin protein;
    (ii) contacting the ubiqttitin-conjugating system with a candidate agent;
    (iii) measuring a level of ubiquitination of the cyclin protein in the presence of the candidate agent; and
    (iv) comparing the measured level of ubiquitination of the cyclin protein in the presence of the candidate agent with a level of ubiquitination of the cyclin protein in the absence of the candidate agent,
wherein a decrease in ubiquitination of the cyclin protein in the presence of the candidate agent is indicative of an inhibitor of ubiquifination of the cyclin protein.

12. The assay of claim 11, wherein the ubiquitin is provided in a form selected from the group consisting of:
    (i) an unconjugated ubiquitin, in which case the ubiquitin-conjugating system further comprises an E1 ubiquitin-activating enzyme (E1), an E2 ubiquifin-conjugating enzyme (E2), and adenosine triphosphate;
    (ii) an activated E1:ubiquitin complex, in which case the ubiquitin-conjugating system further comprises an E2; and
    (iii) an activated E2:ubiquitin complex.

13. The assay of claim 11, wherein the complex which includes a CDC27 and a CDC16 is a 20S complex isolated from a mitotically-regulated cell lysate fraction.

14. The assay of claim 11, wherein the E2 enzyme is selected from the group consisting of UBC4 and UBC5.

15. The assay of claim 11, wherein the cyclin is cyclin B.

16. The assay of claim 11, wherein at least one of the ubiquitin and the cyclin protein comprises a detectable label, and the level of ubiquitin-conjugated cyclin protein is quantified by detecting the label in at least one of the cyclin protein, the ubiquitin, and the ubiquitin-conjugated cyclin protein.

17. An assay for identifying an inhibitor of ubiquitin-mediated proteolysis of a cyclin protein, comprising:
    (i) providing a ubiquitin-conjugating system, which system comprises a cyclin protein, a mitotic destruction complex including a CDC27 and a CDC16, an E2 enzyme selected from the group consisting of UBC4 and UBC5, and ubiquitin, under conditions which promote ubiquitination of the cyclin protein, wherein at least one of the CDC27, of CDC16 is provided to the system as a purified, semi-purified or-recombinant preparation;
    (ii) contacting the ubiquitin-conjugating system with a candidate agent;
    (iii) measuring a level of ubiquitination of the cyclin protein in the presence of the candidate agent; and
    (iv) comparing the measured level of ubiquitination in the presence of the candidate agent with a level of ubiquitination of the cyclin protein in the absence of the candidate agent,
wherein a decrease in ubiquitination of the cyclin protein in the presence of the candidate agent is indicative of an inhibitor of ubiquitination of the cyclin protein.

18. The assay of claim 17, wherein the cyclin protein is a cyclin including a destruction box.

19. The assay of claim 17, wherein the cyclin protein is a cyclin B.

20. The assay of claim 17, wherein the ubiquitin is provided in a form selected from the group consisting of:
    (i) an unconjugated ubiquitin, in which case the ubiquitin-conjugating system further comprises an E1 ubiquitin-activating enzyme (E1), an E2 ubiquitin-conjugating enzyme (E2), and adenosine triphosphate;
    (ii) an activated E1:ubiquitin complex, in which case the ubiquitin-conjugating system further comprises an E2; and
    (iii) an activated E2:ubiquitin complex.

21. The assay of claim 17, wherein mitotic destruction complex is a 20S complex isolated from a mitotically-regulated cell lysate fraction.

22. The assay of claim 17, wherein at least one of the ubiquitin and the cyclin protein comprises a detectable label, and the level of ubiquitin-conjugated cyclin protein is quantified by detecting the label in at least one of the cyclin protein, the ubiquitin, and the ubiquitin-conjugated cyclin protein.

23. The assay of claim 17, wherein the amount of ubiquitin-conjugated cyclin protein is quantified by an immunoassay.

24. An assay for identifying an inhibitor of ubiquitin-mediated proteolysis of a cell-cycle regulatory protein, comprising:
    (i) providing a ubiquitin-conjugating system, comprising semi-purified cell extract including a cell-cycle regulatory protein, a mitotic destruction complex including a CDC27 and a CDC16, an E2 enzyme, and ubiquitin, under conditions which promote ubiquitination of the regulatory protein, and wherein the semi-purified cell extract is charged with at least one component of a ubiquitin-conjugation pathway; wherein one or both of the CDC27 or CDC16 is provided to the system as a purified, semipurified or recombinant preparation;

(ii) contacting the ubiquitin-conjugating system with a candidate agent;

(iii) measuring a level of ubiquitination of the regulatory protein in the presence of the candidate agent; and (iv) comparing the measured level of ubiquitination in the presence of the candidate agent with a level of ubiquitination of the regulatory protein in the absence of the candidate agent, wherein a decrease in ubiquitination of the regulatory protein in the presence of the candidate agent is indicative of an inhibitor of ubiquitination of the regulator, protein.

25. The assay of claim 24, wherein the regulatory protein is selected from the group consisting of a cyclin, p53, myc, and fos.

26. The assay of claim 24, wherein the complex which includes a CDC27 and a CDC16 is a 20S complex.

27. The assay of claim 24, wherein the E2 enzyme is selected from the group consisting of UBC4 and UBC5.

28. The assay of claim 24, wherein at least one of the ubiquitin and the regulatory protein comprises a detectable label, and the level of ubiquitin-conjugated regulatory protein is quantified by detecting the label in at least one of the regulatory protein, the ubiquitin, and the ubiquitin-conjugated regulatory protein.

29. An assay for identifying an agent which competitively inhibits binding of a mitotic destruction complex with a cell-cycle regulatory protein, comprising:

(i) forming a mixture comprising: at least one protein component of a mitotic destruction complex (MDC), said protein component being selected from the group consisting of CDC27 and CDC16, a cell-cycle regulatory protein which binds to said MDC, and a candidate agent;

(ii) measuring a level of binding between the regulatory protein and the MDC in the presence of the candidate agent; and (iv) comparing the measured level of binding in the presence of the candidate agent with a level of binding of the regulatory protein to the MDC in the absence of the candidate agent, wherein a statistically significant decrease in binding of the regulatory protein to the MDC in the presence of the candidate agent is indicative of an agent which competitively inhibits binding of a mitotic destruction complex with a cell-cycle regulatory protein.

30. An assay for identifying an agent which competitively inhibits binding of a mitotic destruction complex with a ubiquitin conjugating enzyme, comprising:

(i) forming a mixture comprising: at least one protein component of a mitotic destruction complex (MDC), said protein component being selected from the group consisting of CDC27 and CDC16, an E2 enzyme which binds to said MDC, and a candidate agent;

(ii) measuring a level of binding between the E2 enzyme and the MDC in the presence of the candidate agent; and (iv) comparing the measured level of binding in the presence of the candidate agent with a level of binding of the E2 enzyme to the MDC in the absence of the candidate agent, wherein a statistically significant decrease in binding of the E2 enzyme to the MDC in the presence of the candidate agent is indicative of an agent which competitively inhibits binding of a mitotic destruction complex with an E2 enzyme.

* * * * *

UNITED STATES PATENT AND TRADEMARK OFFICE
CERTIFICATE OF CORRECTION

PATENT NO. : 5,726,025
DATED : March 10, 1998
INVENTOR(S) : Marc W. Kirschner, Randall W. King, and Jan-Michael Peters It is certified that error appears in the above-identified patent and that said Letters Patent is hereby corrected as shown below:

At column 1, line 6: insert

-- This invention was made with Government support under Grant Nos. GM39023 and GM26875 awarded by the National Institutes of Health. The Government has certain rights to the invention --

Signed and Sealed this

First Day of September, 1998

Attest:

Attesting Officer

BRUCE LEHMAN

Commissioner of Patents and Trademarks